United States Patent
Watanabe et al.

(10) Patent No.: US 9,890,165 B2
(45) Date of Patent: Feb. 13, 2018

(54) TRICYCLIC COMPOUND AND JAK INHIBITOR

(71) Applicant: NISSAN CHEMICAL INDUSTRIES, LTD., Chiyoda-ku (JP)

(72) Inventors: Tsuneo Watanabe, Funabashi (JP); Keiji Takahashi, Funabashi (JP); Keishi Hayashi, Funabashi (JP); Takanori Nakamura, Shiraoka (JP); Masataka Minami, Funabashi (JP); Kazunori Kurihara, Funabashi (JP); Akio Yamamoto, Funabashi (JP); Takuya Nishimura, Funabashi (JP); Miyuki Uni, Funabashi (JP); Toshihiko Kamiyama, Funabashi (JP); Shunsuke Iwamoto, Funabashi (JP)

(73) Assignee: NISSAN CHEMICAL INDUSTRIES, LTD., Chiyoda-ku (JP)

( * ) Notice: Subject to any disclaimer, the term of this patent is extended or adjusted under 35 U.S.C. 154(b) by 0 days.

(21) Appl. No.: 15/307,036

(22) PCT Filed: May 11, 2015

(86) PCT No.: PCT/JP2015/063504
§ 371 (c)(1),
(2) Date: Oct. 27, 2016

(87) PCT Pub. No.: WO2015/174376
PCT Pub. Date: Nov. 19, 2015

(65) Prior Publication Data
US 2017/0044161 A1    Feb. 16, 2017

(30) Foreign Application Priority Data
May 14, 2014    (JP) .................................. 2014-100712

(51) Int. Cl.
*A61K 31/4375* (2006.01)
*A61K 31/519* (2006.01)
*C07D 471/14* (2006.01)

(52) U.S. Cl.
CPC ........ *C07D 471/14* (2013.01); *A61K 31/4375* (2013.01); *A61K 31/519* (2013.01); *Y02P 20/55* (2015.11)

(58) Field of Classification Search
CPC .............. A61K 31/4375; A61K 31/519; C07D 471/14; Y02P 20/55
See application file for complete search history.

(56) References Cited

U.S. PATENT DOCUMENTS 9,216,999 B2    12/2015    Hayashi et al.
2011/0190489 A1    8/2011    Wishart et al.
(Continued)

FOREIGN PATENT DOCUMENTS

JP    2013-512282 A    4/2013
JP    2013-517220 A    5/2013
(Continued)

OTHER PUBLICATIONS

West, Anthony R., Solid State Chemistry and Its Applications, Wiley, New York, 1988, 358.*
(Continued)

*Primary Examiner* — Erich A Leeser
(74) *Attorney, Agent, or Firm* — Oblon, McClelland, Maier & Neustadt, L.L.P.

(57) ABSTRACT

Novel tricyclic compounds which have JAK inhibitory activities are useful for prevention, treatment or improvement of autoimmune diseases, inflammatory diseases and allergic diseases are provided.

Novel tricyclic compound represented by the formula (I), the formula (II) or the formula (III) (wherein: each of $A^1$, $A^2$ and $A^3$ is a cyclohexane-1,4-diyl group or the like; each of $L^1$, $L^2$ and $L^3$ is a methylene group or the like; each of $X^1$ and $X^3$ is O or NH; each of $R^1$ and $R^3$ is a cyano $C_{1-6}$ haloalkyl group or the like; and $R^2$ is an aromatic heterocyclic group), a tautomer or pharmaceutically acceptable salt of the compound or a solvate thereof.

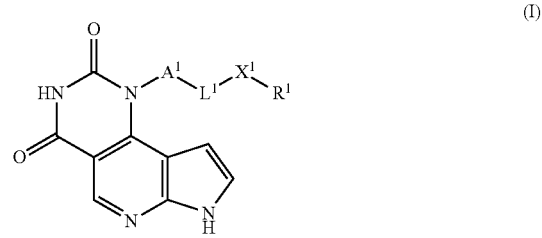

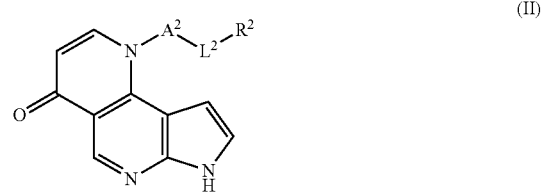

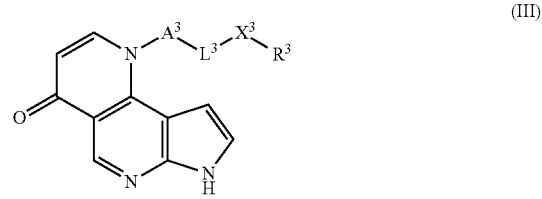

18 Claims, No Drawings

(56) References Cited

U.S. PATENT DOCUMENTS

| | | |
|---|---|---|
| 2011/0201593 A1 | 8/2011 | Babu et al. |
| 2014/0200344 A1 | 7/2014 | Hayashi et al. |
| 2014/0349970 A1 | 11/2014 | Wishart et al. |
| 2016/0102102 A1 | 4/2016 | Hayashi et al. |

FOREIGN PATENT DOCUMENTS

| | | | |
|---|---|---|---|
| WO | 01/42246 A2 | 6/2001 | |
| WO | 2007/007919 A2 | 1/2007 | |
| WO | 2007/077949 A1 | 7/2007 | |
| WO | 2008/084861 A1 | 7/2008 | |
| WO | 2009/152133 A1 | 12/2009 | |
| WO | 2010/119875 A1 | 10/2010 | |
| WO | 2011/045702 A1 | 4/2011 | |
| WO | 2011/068881 A1 | 6/2011 | |
| WO | 2011/068899 A1 | 6/2011 | |
| WO | 2011/075334 A1 | 6/2011 | |
| WO | 2011/086053 A1 | 7/2011 | |
| WO | 2012/085176 A1 | 6/2012 | |
| WO | 2012/127506 A1 | 9/2012 | |
| WO | 2012/149280 A2 | 11/2012 | |
| WO | 2013/024895 A1 | 2/2013 | |
| WO | WO 2013/024895 * | 2/2013 | ........... C07D 487/14 |
| WO | 2014/123167 A1 | 8/2014 | |

OTHER PUBLICATIONS

International Search Report dated Jul. 14, 2015 in PCT/JP2015/063504 filed May 11, 2015.

P. J. Murray, "The JAK-STAT Signaling Pathway: Input and Output Integration," The Journal of Immunology, 2007, vol. 178, pp. 2623-2629.

J. Staerk, et al., "JAK2, the JAK2 V617F mutant and cytokine receptors," Pathologie Biologie, 2007, vol. 55, pp. 88-91.

J. Yoo, et al., "JAK2 V617F/C618R mutation in a patient with polycythemia vera: A case study and review of the literature," Cancer Genetics and Cytogenetics, 2009, vol. 189, pp. 43-47.

W. Vainchenker, et al., "JAKs in pathology: Role of Janus kinases in hematopoietic malignancies and immunodeficiencies," Seminars in Cell & Developmental Biology, 2008, vol. 19, pp. 385-393.

J. J. O'Shea, et al., "Cytokine Signaling in 2002: New Surprises in the Jak/Stat Pathway," Cell. Apr. 2002, vol. 109, pp. S121-S131.

K. Ozaki, et al., "A Critical Role for IL-21 in Regulating Immunoglobulin Production," Science, Nov. 22, 2002, vol. 298, pp. 1630-1634.

P. Macchi, et al., "Mutations of Jak-3 gene in patients with autosomal severe combined immune deficiency (SCID)," Nature, Sep. 7, 1995, vol. 377, pp. 65-66.

S. M. Russell, et al., "Mutation of Jak3 in a Patient with SCID: Essential Role of Jak3 in Lymphoid Development," Science, Nov. 3, 1995, vol. 270, pp. 797-800.

E. Bournazou, et al., "Targeting the tumor microenvironment JAK-STAT3 signaling," JAK-STAT, 2013, vol. 2, Issue 2, pp. e23828-1 to e23828-8.

J. M. Kremer, et al., "The Safety and Efficacy of a JAK Inhibitor in Patients With Active Rheumatoid Arthritis Results of a Double-Blind, Placebo-Controlled Phase IIa Trial of Three Dosage Levels of CP-690,550 Versus Placebo," Arthritis Rheumatism, Jul. 2009, vol. 60, No. 7, pp. 1895-1905.

M. G. Boy, et al., "Double-Blind, Placebo-Controlled, Dose-Escalation Study to Evaluate the Pharmacologic Effect of CP-690,550 in Patients with Psoriasis," Journal of Investigative Dermatology, 2009, vol. 129, pp. 2299-2302.

P. S. Changelian, et al., "Prevention of Organ Allograft Rejection by a Specific Janus Kinase 3 Inhibitor," Science, Oct. 31, 2003, vol. 302, No. 5646, pp. 875-878.

E. Kudlacz, et al., "The JAK-3 inhibitor CP-690550 is a potent anti-inflammatory agent in a murine model of pulmonary eosinophilia," European Journal of Pharmacology, 2008, vol. 582, pp. 154-161.

* cited by examiner

TRICYCLIC COMPOUND AND JAK INHIBITOR

TECHNICAL FIELD

The present invention relates to novel tricyclic compounds having JAK inhibitory activities.

BACKGROUND ART

The JAK (Janus kinase) family is a tyrosine kinase family consisting of four members, JAK1, JAK2, JAK3 and Tyk (Tyrosine kinase) 2 and plays an important role in cytokine signaling by phosphorylating STATs (signal transducers and activators of transcription).

Analyses of JAK1 knockout mice and JAK1-deficient cells suggest involvement of JAK1 in various receptor-mediated signaling pathways such as IFN (Interferon)α, IFNβ, IFNγ, IL (interleukin)-2, IL-4, IL-6, IL-7 and IL-15 signaling (Non-Patent Document 1). Therefore, regulation of inflammatory responses via these signaling pathways is therapeutically promising for treatment of diseases involving macrophage and lymphocyte activation such as autoimmune diseases and acute and chronic organ transplant rejection.

Analyses of JAK2 knockout mice and JAK2-deficient cells suggest involvement of JAK2 in various receptor-mediated signaling pathways such as EPO (Erythropoietin), TPO (thrombopoietin), IFNγ, IL-3 and GM-CSF (Granulocyte Macrophage colony-stimulating Factor) signaling (Non-Patent Documents 2, 3 and 4). These signaling pathways are supposed to mediate differentiation of erythrocyte or thrombocyte progenitor cells in bone marrow.

Meanwhile, it is suggested that a substitution of phenylalanine-617 with valine in JAK2 is associated with myeloproliferative diseases (Non-Patent Document 2). Therefore, regulation of differentiation of myeloid progenitor cells via these mechanisms is therapeutically promising for treatment of chronic myeloproliferative diseases.

JAK3 plays an important role in various receptor-mediated signaling pathways such as IL-2, IL-4, IL-7, IL-9, IL-15 and IL-21 signaling by noncovalently associating with the common γ chain (Non-Patent Documents 5 and 6).

Lowered JAK3 protein levels or defects in the common γ chain gene observed in patients with an immunodeficiency called X-linked Severe Combined Immuno Deficiency (XS-CID) suggest that blocking of the JAK3 signaling pathway leads to immunosuppression (Non-Patent Documents 7 and 8).

Animal experiments indicate the importance of JAK3 not only in maturation of B- and T-lymphocytes but also in maintenance of T-lymphocyte functions. Therefore, regulation of immune responses via this mechanism is a promising therapy for T-cell lymphoproliferative diseases such as organ transplant rejection and autoimmune diseases.

In leukemia and lymphoma cells and cells of many solid cancers, JAKs and STATs are activated constitutively (Non-Patent Document 9). This indicates that JAK inhibitors are expected to cure cancer and leukemia by suppressing cancer cell growth.

The JAK inhibitor CP-690, 550 is reported to have improved the pathology of rheumatoid arthritis and psoriasis in clinical tests (Non-Patent Documents 10 and 11) and suppressed rejection in a monkey model of kidney transplantation and airway inflammation in a murine asthma model (Non-Patent Documents 12 and 13).

From these findings, immunosuppression by JAK inhibitors is considered to be useful for prevention or treatment of organ transplant rejection and post-transplant graft-versus-host reaction, autoimmune diseases and allergic diseases. Although compounds having JAK inhibitory action other than CP-690, 550 have been reported (Patent Documents 1 to 15), development of more of such compounds is demanded.

Patent Document 15 reports some tricyclic heterocyclic compounds having JAK inhibitory action, but has no specific description of the compounds of the present invention.

PRIOR ART DOCUMENTS

Patent Documents

Patent Document 1: WO2001/042246
Patent Document 2: WO2007/007919
Patent Document 3: WO2007/077949
Patent Document 4: WO2008/084861
Patent Document 5: WO2009/152133
Patent Document 6: WO2010/119875
Patent Document 7: WO2011/045702
Patent Document 8: WO2011/068881
Patent Document 9: WO2011/068899
Patent Document 10: WO2011/075334
Patent Document 11: WO2011/086053
Patent Document 12: WO2012/085176
Patent Document 13: WO2012/127506
Patent Document 14: WO2012/149280
Patent Document 15: WO2013/024895

NON-PATENT DOCUMENTS

Non-Patent Document 1: J. Immunol., 2007, 178, pp. 2623-2629
Non-Patent Document 2: Pathol. Biol., 2007, 55, pp. 88-91
Non-Patent Document 3: Cancer Genet. Cytogenet., 2009, 189, pp. 43-47
Non-Patent Document 4: Semin. Cell. Dev. Biol., 2008, 19, pp. 385-393
Non-Patent Document 5: Cell, 2002, 109, pp. S121-131
Non-Patent Document 6: Science, 2002, 298, pp., 1630-1634
Non-Patent Document 7: Nature, 1995, 377, pp. 65-68
Non-Patent Document 8: Science, 1995, 270, pp. 797-800
Non-Patent Document 9: JAK-STAT., 2013, 2, e23828
Non-Patent Document 10: Arthritis Rheum., 2009, 60, pp. 1895-1905
Non-Patent Document 11: J Invest. Dermatol., 2009, 129, pp. 2299-2302
Non-Patent Document 12: Science, 2003, 302, pp. 875-878
Non-Patent Document 13: Eur. J. Pharmacol., 2008, 582, pp. 154-161

DISCLOSURE OF THE INVENTION

Technical Problem

The object of the present invention is to provide novel drug compounds having excellent JAK inhibitory activities useful for prevention, treatment or improvement of autoimmune diseases, inflammatory diseases and allergic diseases.

Solution to Problems

As a result of their extensive research in search of new low-molecular-weight compounds having JAK inhibitory activities, the present inventors discovered that the compounds of the present invention have high inhibitory activities on cytokine signaling via the JAK family in rat or human whole blood and accomplished the present invention. Namely, the present invention provides the following.

(1) A compound represented by the formula (I):

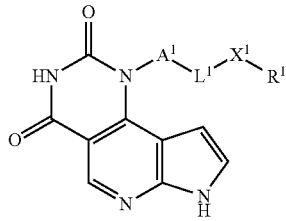

(I)

[wherein $A^1$ is a $C_{3-7}$ cycloalkylene group, $L^1$ is a $C_{1-6}$ alkylene group, $X^1$ is O or NH, and when $X^1$ is O, $R^1$ is a $C_{1-6}$ haloalkyl group, a cyano $C_{1-6}$ haloalkyl group or a cyano $C_{1-6}$ alkyl group, and when $X^1$ is NH, $R^1$ is a cyano $C_{1-6}$ haloalkyl group or a cyano $C_{1-6}$ alkyl group], a tautomer or pharmaceutically acceptable salt of the compound or a solvate thereof.

(2) The compound according to (1), wherein $L^1$ is a methylene group, a tautomer or pharmaceutically acceptable salt of the compound or a solvate thereof.

(3) The compound according to (1) or (2), wherein $A^1$ is a cyclohexanediyl group, a tautomer or pharmaceutically acceptable salt of the compound or a solvate thereof.

(4) The compound according to any one of (1) to (3), wherein $X^1$ is O, a tautomer or pharmaceutically acceptable salt of the compound or a solvate thereof.

(5) The compound according to (4), wherein $R^1$ is a $C_{1-4}$ haloalkyl group, a tautomer or pharmaceutically acceptable salt of the compound or a solvate thereof.

(6) The compound according to (4), wherein $R^1$ is a 3,3,3-trifluoropropyl group, a tautomer or pharmaceutically acceptable salt of the compound or a solvate thereof.

(7) 1-{trans-4-[(3,3,3-Trifluoropropoxy)methyl]cyclohexyl}-1H-pyrrolo[3',2':5,6]pyrido[4,3-d]pyrimidine-2,4(3H,7H)-dione, a tautomer or pharmaceutically acceptable salt of the compound or a solvate thereof.

(8) The compound according to any one of (1) to (3), wherein $X^1$ is NH, a tautomer or pharmaceutically acceptable salt of the compound or a solvate thereof.

(9) The compound according to (8), wherein $R^1$ is a cyano $C_{1-4}$ haloalkyl group, a tautomer or pharmaceutically acceptable salt of the compound or a solvate thereof.

(10) The compound according to (8), wherein $R^1$ is a 3-cyano-1,1,1-trifluoropropan-2-yl group, a tautomer or pharmaceutically acceptable salt of the compound or a solvate thereof.

(11) 3-({[trans-4-(2,4-Dioxo-2,3,4,7-tetrahydro-1H-pyrrolo[3',2':5,6]pyrido[4,3-d]pyrimidin-1-yl)cyclohexyl]methyl}amino)-4,4,4-trifluorobutanenitrile, a tautomer or pharmaceutically acceptable salt of the compound or a solvate thereof.

(12) (R)-3-({[trans-4-(2,4-Dioxo-2,3,4,7-tetrahydro-1H-pyrrolo[3',2':5,6]pyrido[4,3-d]pyrimidin-1-yl)cyclohexyl]methyl}amino)-4,4,4-trifluorobutanenitrile, a tautomer or pharmaceutically acceptable salt of the compound or a solvate thereof.

(13) A compound represented by the formula (II):

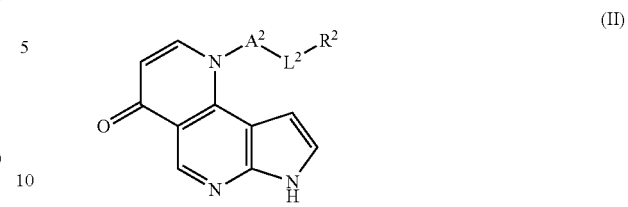

(II)

[wherein $A^2$ is a $C_{3-7}$ cycloalkylene group, $L^2$ is a $C_{1-6}$ alkylene group, and $R^2$ is a 5 to 10-membered aromatic heterocyclic group (the heterocyclic group may be substituted with one or two identical or different substituents independently selected from the group consisting of halogen atoms, $C_{1-4}$ alkyl groups and $C_{1-4}$ haloalkyl groups)], a tautomer or pharmaceutically acceptable salt of the compound or a solvate thereof.

(14) The compound according to (13), wherein $L^2$ is a methylene group, a tautomer or pharmaceutically acceptable salt of the compound or a solvate thereof.

(15) The compound according to (13) or (14), wherein $A^2$ is a cyclohexanediyl group, a tautomer or pharmaceutically acceptable salt of the compound or a solvate thereof.

(16) The compound according to any one of (13) to (15) wherein $R^2$ is a 5 to 6-membered nitrogen-containing aromatic heterocyclic group (the heterocyclic group may be substituted with one or two identical or different substituents independently selected from the group consisting of halogen atoms, methyl groups and trifluoromethyl groups), a tautomer or pharmaceutically acceptable salt of the compound or a solvate thereof.

(17) The compound according to any one of (13) to (16), wherein $R^2$ is a pyrazolyl group (the pyrazolyl group may be substituted with one or two identical or different substituents independently selected from the group consisting of halogen atoms, methyl groups and trifluoromethyl groups), a tautomer or pharmaceutically acceptable salt of the compound or a solvate thereof.

(18) 1-{trans-4-[(4-Methyl-1H-pyrazol-1-yl)methyl]cyclohexyl}-1H-pyrrolo[2,3-h][1,6]naphthyridin-4(7H)-one, a tautomer or pharmaceutically acceptable salt of the compound or a solvate thereof.

(19) A compound represented by the formula (III):

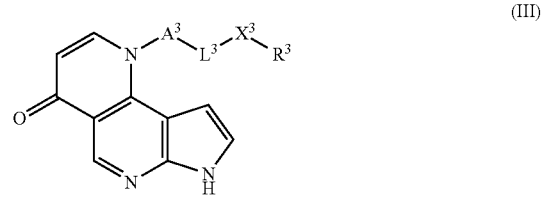

(III)

[wherein $A^3$ is a $C_{3-7}$ cycloalkylene group, $L^3$ is a $C_{1-6}$ alkylene group, $X^3$ is O or NH, and when $X^3$ is O, $R^3$ is a $C_{1-6}$ haloalkyl group, a cyano $C_{1-6}$ haloalkyl group or a cyano $C_{1-6}$ alkyl group, and when $X^3$ is NH, $R^3$ is a cyano $C_{1-6}$ haloalkyl group or a cyano $C_{1-6}$ alkyl group], a tautomer or pharmaceutically acceptable salt of the compound or a solvate thereof.

(20) The compound according to (19), wherein $L^3$ is a methylene group, a tautomer or pharmaceutically acceptable salt of the compound or a solvate thereof.

(21) The compound according to (19) or (20), wherein $A^3$ is a cyclohexanediyl group, a tautomer or pharmaceutically acceptable salt of the compound or a solvate thereof.

(22) The compound according to any one of (19) to (21), wherein $X^3$ is O a tautomer or pharmaceutically acceptable salt of the compound or a solvate thereof.

(23) The compound according to (22), wherein $R^3$ is a $C_{1-4}$ haloalkyl group or a cyano $C_{1-4}$ haloalkyl group, a tautomer or pharmaceutically acceptable salt of the compound or a solvate thereof.

(24) The compound according to (22), wherein $R^3$ is a 2,2,2-trifluoroethyl group or a 3,3-trifluoropropyl group, a tautomer or pharmaceutically acceptable salt of the compound or a solvate thereof.

(25) The compound according to (22), wherein $R^3$ is a 3-cyano-1,1,1-trifluoropropan-2-yl group or a 2-cyano-1,1,1-trifluoropropan-2-yl group, a tautomer or pharmaceutically acceptable salt of the compound or a solvate thereof.

(26) 1-{trans-4-[(2,2,2-Trifluoroethoxy)methyl]cyclohexyl}-1H-pyrrolo[2,3-h][1,6]naphthyridin-4(7H)-one, a tautomer or pharmaceutically acceptable salt of the compound or a solvate thereof.

(27) 1-{trans-4-[(3,3,3-Trifluoropropoxy)methyl]cyclohexyl}-1H-pyrrolo[2,3-h][1,6]naphthyridin-4(7H)-one, a tautomer or pharmaceutically acceptable salt of the compound or a solvate thereof.

(28) 4,4,4-Trifluoro-3-{[trans-4-(4-oxo-4,7-dihydro-1H-pyrrolo[2,3-h][1,6]naphthyridin-1-yl)cyclohexyl]methoxy}butanenitrile, a tautomer or pharmaceutically acceptable salt of the compound or a solvate thereof.

(29) (R)-4,4,4-Trifluoro-3-{[trans-4-(4-oxo-4,7-dihydro-1H-pyrrolo[2,3-h][1,6]naphthyridin-1-yl)cyclohexyl]methoxy}butanenitrile, a tautomer or pharmaceutically acceptable salt of the compound or a solvate thereof.

(30) The compound according to any one of (19) to (21), wherein $X^3$ is NH, a tautomer or pharmaceutically acceptable salt of the compound or a solvate thereof.

(31) The compound according to (30), wherein $R^3$ is a cyano haloalkyl group, a tautomer or pharmaceutically acceptable salt of the compound or a solvate thereof.

(32) The compound according to (30), wherein $R^3$ is a 3-cyano-1,1,1-trifluoropropan-2-yl group, a tautomer or pharmaceutically acceptable salt of the compound or a solvate thereof.

(33) 4,4,4-Trifluoro-3-({[trans-4-(4-oxo-4,7-dihydro-1H-pyrrolo[2,3-h][1,6]naphthyridin-1-yl)cyclohexyl]methyl}amino)butanenitrile, a tautomer or pharmaceutically acceptable salt of the compound or a solvate thereof.

(34) (R)-4,4,4-Trifluoro-3-({[trans-4-(4-oxo-4,7-dihydro-1H-pyrrolo[2,3-h][1,6]naphthyridin-1-yl)cyclohexyl]methyl}amino)butanenitrile, a tautomer or pharmaceutically acceptable salt of the compound or a solvate thereof.

(35) A JAK inhibitor containing the compound as defined in any one of (1) to (34), a tautomer or a pharmaceutically acceptable salt of the compound or a solvate thereof, as an active ingredient.

(36) A preventive, therapeutic or improving agent for diseases against which inhibition of JAK is effective, which contains the compound as defined in any one of (1) to (34), a tautomer or pharmaceutically acceptable salt of the compound or a solvate thereof, as an active ingredient.

(37) A therapeutic agent for rheumatoid arthritis, which contains the compound as defined in any one of (1) to (34), a tautomer or pharmaceutically acceptable salt of the compound or a solvate thereof, as an active ingredient.

(38) Medicament containing the compound as defined in any one of (1) to (34), a tautomer or a pharmaceutically acceptable salt of the compound or a solvate thereof, as an active ingredient.

Advantageous Effect(s) of Invention

The present invention has made it possible to provide novel tricyclic compounds which have excellent JAK inhibitory action and are especially useful for prevention, treatment or improvement of autoimmune diseases, inflammatory diseases and allergic diseases.

DESCRIPTION OF EMBODIMENT(S)

Now, the present invention will be described in further detail.

In the present invention, "n-" denotes normal, "i-" denotes iso, "s-" and "sec" denote secondary, "t-" and "tert-" denote tertiary, "c-" denotes cyclo, "o-" denotes ortho, "m-" denotes meta, "p-" denotes para, "cis-" denotes a cis isomer, "trans-" denotes a trans isomer, "rac" and "racemate" denote racemate, "Ph" denotes phenyl, "Py" denotes pyridyl, "Me" denotes methyl, "Et" denotes ethyl, "Pr" denotes propyl, "Bu" denotes butyl, "Boc" denotes tertiary-butoxycarbonyl, "Ms" denotes methanesulfonyl, "Tf" denotes trifluoromethanesulfonyl, "Ts" denotes p-toluenesulfonyl, "SEM" denotes [2-(trimethylsilyl) ethoxy]methyl, "TIPS" denotes triisopropylsilyl, "TMS" denotes trimethylsilyl, and "Ac" denotes acetyl.

First, the terms used herein for description of chemical structures will be explained.

A "halogen atom" is a fluorine atom, a chlorine atom, a bromine atom or an iodine atom.

A "$C_{1-4}$ alkyl group" is a methyl group, an ethyl group, a n-propyl group, an isopropyl group, a n-butyl group, an isobutyl group, a s-butyl group or a t-butyl group.

A "$C_{1-6}$ alkyl group" is a linear or branched alkyl group containing one to six carbon atoms, and in addition to the above-mentioned specific "$C_{1-4}$ alkyl group", a n-pentyl group, n-hexyl group or the like may be mentioned.

A "cyano $C_{1-6}$ alkyl group" is a group derived from the above-mentioned "$C_{1-6}$ alkyl group" by replacing one or more hydrogen atom(s) at arbitrary position(s) by one or more cyano groups. As specific examples, a cyanomethyl group, a 2-cyanoethyl group, a 1-cyanopropan-2-yl group, a 2-cyanopropan-2-yl group, a 3-cyanopropyl group, a 1,3-dicyanopropan-2-yl group, a 1-cyanobutan-2-yl group, a 4-cyanobutyl group, a 5-cyanopentyl group, a 6-cyanohexyl group and the like may be mentioned.

A "$C_{1-4}$ haloalkyl group" is a group derived from the above-mentioned "$C_{1-4}$ alkyl group" by replacing one or more hydrogen atom(s) at arbitrary position(s) by one or more identical or different halogen atoms selected from the group consisting of fluorine atom, chlorine atom, bromine atom and iodine atom. As specific examples, a trifluoromethyl group, a pentafluoroethyl group, a 2,2,2-trifluoroethyl group, a 3,3,3-trifluoropropyl group, a 4,4,4-trifluorobutyl group, a 4,4,4-trifluorobutan-2-yl group, a 2,2-difluoroethyl group, a 2,2-difluoropropyl group, a 2-chloroethyl group, a 3-bromopropyl group, a 4-iodobutyl group and the like may be mentioned.

A "$C_{1-6}$ haloalkyl group" is a group derived from the above-mentioned "$C_{1-6}$ alkyl group" by replacing one or more hydrogen atom(s) at arbitrary position(s) by one or more identical or different halogen atoms selected from the group consisting of fluorine atom, chlorine atom, bromine atom and iodine atom. As specific examples, in addition to the above-mentioned specific "$C_{1-4}$ haloalkyl group", a 5,5,5-trifluoropentyl group, a 6,6,6-trifluorohexyl group, a 5-chloropentyl group, a 6-bromohexyl group and the like may be mentioned.

A "cyano $C_{1-4}$ haloalkyl group" is a group derived from the above-mentioned "$C_{1-4}$ haloalkyl group" by replacing one or more hydrogen atom(s) at arbitrary position(s) by one or more cyano groups. As specific examples, a 1-cyano-2,2,2-trifluoroethyl group, a 3-cyano-1,1,1-trifluoropropan-2-yl group, a 2-cyano-1,1,1-trifluoropropan-2-yl group a 4-cyano-1,1,1-trifluorobutan-2-yl group and the like may be mentioned.

A "cyano 01-6 haloalkyl group" is a group derived from the above-mentioned "$C_{1-6}$ haloalkyl group" by replacing one or more hydrogen atom(s) at arbitrary position(s) by one or more cyano groups. As specific examples, in addition to the above-mentioned specific "cyano $C_{1-4}$ haloalkyl group", a 5-cyano-1,1,1-trifluoropentan-2-yl group, a 6-cyano-1,1,1-trifluoronexan-2-yl group and the like may be mentioned.

A "$C_{3-7}$ cycloalkane" is a monocyclic, fused, bridged or Spiro aliphatic hydrocarbon ring having 3 to 7 ring-constituting carbon atoms. As specific examples, cyclopropane, cyclobutane, cyclopentane, cyclohexane, cycloheptane, bicyclo[2.2.1]heptane and the like may be mentioned.

A "$C_{3-7}$ cycloalkyl group" is a monovalent group derived from the above-mentioned "$C_{3-7}$ cycloalkane" by removing a hydrogen atom at an arbitrary position. As specific examples, a cyclopropyl group, a cyclobutyl group, a cyclopentyl group, a cyclohexyl group, a cycloheptyl group, a bicyclo[2.2.1]heptan-1-yl group, a bicyclo[22.1]heptan-2-yl group, a bicyclo[2.2.1]heptan-7-yl group and the like may be mentioned.

A "$C_{1-6}$ alkylene group" is a bivalent group derived from the above-mentioned "$C_{1-6}$ alkyl group" by removing a hydrogen atom at an arbitrary position. As specific examples, a methylene group, an ethylene group, a propane-1,3-diyl group, a propane-1,2-diyl group, a 2,2-dimethylpropane-1,3-diyl group, a hexane-1,6-diyl group, a 3-methylbutane-1,2-diyl group and the like may be mentioned.

A "$C_{3-7}$ cycloalkylene group" is a bivalent group derived from the above-mentioned "$C_{3-7}$ cycloalkyl group" by removing a hydrogen atom at an arbitrary position. As specific examples, a cyclopropane-1,2-diyl group, a cyclobutane-1,3-diyl group, a cyclopentane-1,3-diyl group, a cyclohexane-1,4-diyl group, a cyclohexane-1,3-diyl group, a cyclopentane-1,4-diyl group and the like may be mentioned.

A "5 to 10-membered aromatic heterocyclic ring" is a monocyclic or fused aromatic heterocyclic group having 5 to 10 ring-constituting atoms including carbon atoms and one or more hetero atoms (such as nitrogen atoms, oxygen atoms or sulfur atoms). As specific examples, furan, thiophene, pyrrole, imidazole, triazole, tetrazole, thiazole, pyrazole, oxazole, isoxazole, isothiazole, thiadiazole, oxadiazole, pyridine, pyrazine, pyridazine, pyrimidine, triazine, purine, pteridine, quinoline, isoquinoline, naphthylidine, quinoxaline, cinnoline, quinazoline, phthalazine, imidazopyridine, imidazothiazole, imidazooxazole, benzothiazole, benzoxazole, benzimidazole, indole, pyrrolopyridine, thienopyridine, furopyridine, benzothiadiazole, benzoxadiazole, pyridopyrimidine, benzofuran, benzothiophene, thienofuran and the like may be mentioned.

In the case of a "5 to 10-membered aromatic heterocyclic ring" having a C=N double bond, it may be in the form of an N-oxide.

A "5 to 10-membered aromatic heterocyclic group" is a monovalent group derived from the above-mentioned "5 to 10-membered aromatic heterocyclic ring" by removing a hydrogen atom at an arbitrary position.

A "5 to 6-membered aromatic heterocyclic ring" is a monocyclic group having 5 or 6 ring-constituting atoms among the above-mentioned "5 to 10-membered aromatic heterocyclic ring". As specific examples, pyrrole, pyrazole, imidazole, triazole, tetrazole, pyridine, pyridazine, pyrimidine, pyrazine, triazine, furan, thiophene, thiazole, isothiazole, oxazole, isoxazole, oxadiazole, thiadiazole and the like may be mentioned.

A "nitrogen-containing 5 to 6-membered aromatic heterocyclic ring" is an aromatic heterocyclic ring having one or more nitrogen atoms as ring-constituting atoms among the above-mentioned "5 to 6-membered aromatic heterocyclic ring". As specific examples, pyrrole, pyrazole, imidazole, triazole, tetrazole, pyridine, pyridazine, pyrimidine, pyrazine, triazine, thiazole, isothiazole, oxazole, isoxazole, oxadiazole, thiadiazole and the like may be mentioned.

A "nitrogen-containing 5 to 6-membered aromatic heterocyclic group" is a monovalent group derived from the above-mentioned "nitrogen-containing 5 to 6-membered aromatic heterocyclic ring" by removing a hydrogen atom at an arbitrary position.

Next, preferred structures of the respective substituents in the present invention will be mentioned.

$A^1$ is preferably a cyclopentanediyl group, a cyclohexanediyl group or a cycloheptanediyl group, more preferably a cyclohexanediyl group, further preferably a cyclohexane-1,4-diyl group.

$L^1$ is preferably a methylene group or an ethylene group, more preferably a methylene group.

$X^1$ is preferably O or NH.

When $X^1$ is O, $R^1$ is preferably a 2,2,2-trifluoroethyl group, a 3,3,3-trifluoropropyl group, a 3-cyano-1,1,1-trifluoropropan-2-yl group or a 2-cyano-1,1,1-trifluoropropan-2-yl group, more preferably a 3,3,3-trifluoropropyl group.

When $X^1$ is NH, $R^1$ is preferably a 3-cyano-1,1,1-trifluoropropan-2-yl group or a 1-cyanopropan-2-yl group, more preferably a 3-cyano-1,1,1-trifluoropropan-2-yl group.

$A^2$ is preferably a cyclopentanediyl group, a cyclohexanediyl group or a cycloheptanediyl group, more preferably a cyclohexanediyl group, further preferably a cyclohexane-1,4-diyl group.

$L^2$ is preferably a methylene group or an ethylene group, more preferably a methylene group.

$R^2$ is preferably a pyrrolyl group, a thienyl group, a furyl group, a pyrazolyl group, an imidazolyl group, a thiazolyl group, an isothiazolyl group, an oxazolyl group, an isoxazolyl group, a 1H-1,2,4-triazolyl group, a 4H-1,2,4-triazolyl group, a pyridyl group, a pyridazinyl group, a pyrimidinyl group, a pyrazinyl group or a 1,3,5-triazinyl group (each of the pyrrolyl group to the 1,3,5-triazinyl group may be substituted with one or two identical or different substituents independently selected from the group consisting of halogen atoms, methyl groups and trifluoromethyl groups), more preferably a pyrazolyl group, an imidazolyl group, a thiazolyl group, an isothiazolyl group, an oxazolyl group or an isoxazolyl group (each of the pyrazolyl group to the isoxazolyl group may be substituted with one or two identical or different substituents independently selected from the group consisting of halogen atoms, methyl groups and trifluoromethyl groups), further preferably a pyrazolyl group (the pyrazolyl group may be substituted with one or two identical or different substituents independently selected from the group consisting of halogen atoms, methyl groups and trifluoromethyl groups), particularly preferably a pyrazolyl group substituted with a methyl group.

$A^3$ is preferably a cyclopentanediyl group, a cyclohexanediyl group or a cycloheptanediyl group more preferably a cyclohexanediyl group, further preferably a cyclohexane-1,4-diyl group.

$L^3$ is preferably a methylene group or an ethylene group, more preferably a methylene group.

$X^3$ is preferably O or NH.

When $X^3$ is O, $R^3$ is preferably a 2,2,2-trifluoroethyl group, a 3,3,3-trifluoropropyl group, a 3-cyano-1,1,1-trifluoropropan-2-yl group or a 2-cyano-1,1,1-trifluoropropan-2-yl group.

When $X^3$ is NH, $R^3$ is preferably a 3-cyano-1,1,1-trifluoropropan-2-yl group or a 1-cyanopropan-2-yl group, more preferably a 3-cyano-1,1,1-trifluoropropan-2-yl group.

As favorable compounds of the present invention for use as JAK inhibitors and as preventive, therapeutic and/or improving agent for diseases against which inhibition of JAK is effective, the following compounds may be mentioned.

(1) Compounds represented by the formula (I) wherein $A^1$ is a cyclopentanediyl group or a cyclohexanediyl group,
$L^1$ is a methylene group or an ethylene group,
$X^1$ is O, and
$R^1$ is a $C_{1-6}$ haloalkyl group, a cyano $C_{1-6}$ haloalkyl group or a cyano $C_{1-6}$ alkyl group, tautomers or pharmaceutically acceptable salts of the compounds or solvates thereof.

(2) The compounds according to (1), wherein $R^1$ is a 2,2,2-trifluoroethyl group, a 3,3,3-trifluoropropyl group, a 4,4,4-trifluorobutyl group, a 3,3-difluoropropyl group or a 2-cyanoethyl group, tautomers or pharmaceutically acceptable salts of the compounds or solvates thereof.

(3) Compounds represented by the formula (I) wherein $A^1$ is a cyclopentanediyl group or a cyclohexanediyl group,
$L^1$ is a methylene group or an ethylene group,
$X^1$ is NH, and
$R^1$ is a cyano $C_{1-6}$ haloalkyl group or a cyano $C_{1-6}$ alkyl group, tautomers or pharmaceutically acceptable salts of the compounds or solvates thereof.

(4) The compounds according to (3), wherein $R^1$ is a 3-cyano-1,1,1-trifluoropropan-2-yl group, a 4-cyano-1,1,1-trifluorobutan-2-yl group, a 3-cyano-1,1,1-trifluoropropan-2-yl group, a 2-cyano-1,1,1-trifluoropropan-3-yl group, a 2-cyano-1,1,1-trifluoropropan-2-yl group, a 2-cyanoethyl group or a 1-cyano-propan-2-yl group, tautomers or pharmaceutically acceptable salts of the compounds or solvates thereof.

(5) The compounds according to any one of (1) to (4), wherein $L^1$ is a methylene group, tautomers or pharmaceutically acceptable salts of the compounds or solvates thereof.

(6) The compounds according to any one of (1) to (5), wherein $A^1$ is a cyclohexanediyl group, tautomers or pharmaceutically acceptable salts of the compounds or solvates thereof.

(7) Compounds represented by the formula (II) wherein $A^2$ is a cyclopentanediyl group or a cyclohexanediyl group,
$L^2$ is a methylene group or an ethylene group, and
$R^2$ is a 5 to 10-membered aromatic heterocyclic group (the heterocyclic group is substituted with a halogen atom, a methyl group, an ethyl group, a trifluoromethyl group or a 2,2,2-trifluoroethyl group), tautomers or pharmaceutically acceptable salts of the compounds or solvates thereof.

(8) The compounds according to (7), wherein $A^2$ is a cyclohexanediyl group, tautomers or pharmaceutically acceptable salts of the compounds or solvates thereof.

(9) The compounds according to (7) or (8), wherein $L^2$ is a methylene group, tautomers or pharmaceutically acceptable salts of the compounds or solvates thereof.

(10) The compounds according to any one of (7) to (9), wherein $R^2$ is a pyrrolyl group, a thienyl group, a furyl group, a pyrazolyl group, an imidazolyl group, a thiazolyl group, an isothiazolyl group, an oxazolyl group, an isoxazolyl group, a 1H-1,2,4-triazolyl group, a 4H-1,2,4-triazolyl group, a pyridyl group, a pyridazinyl group, a pyrimidinyl group, a pyrazinyl group or a 1,3,5-triazinyl group (each of the pyrrolyl group to the 1,3,5-triazinyl group is substituted with a fluorine atom, a chlorine atom, a bromine atom, a methyl group or a trifluoromethyl group), tautomers or pharmaceutically acceptable salts of the compounds or solvates thereof.

(11) Compounds represented by the formula (III) wherein $A^3$ is a cyclopentanediyl group or a cyclohexanediyl group,
$L^3$ is a methylene group or an ethylene group,
$X^3$ is O, and
$R^3$ is a $C_{1-6}$ haloalkyl group, a cyano $C_{1-6}$ haloalkyl group or a cyano $C_{1-6}$ alkyl group, tautomers or pharmaceutically acceptable salts of the compounds or solvates thereof.

(12) The compounds according to (11), wherein $R^3$ is a 2,2,2-trifluoroethyl group, a 3,3,3-trifluoropropyl group, a 4,4,4-trifluorobutyl group, a 2,2-difluoroethyl group, a 3,3-difluoropropyl group, a 3-cyano-1,1,1-trifluoropropan-2-yl group, a 2-cyano-1,1,1-trifluoropropan-2-yl group, a 2-cyanoethyl group or a 1-cyanopropan-2-yl group, tautomers or pharmaceutically acceptable salts of the compounds or solvates thereof.

(13) Compounds represented by the formula (III) wherein $A^3$ is a cyclopentanediyl group or a cyclohexanediyl group,
$L^3$ is a methylene group or an ethylene group
$X^3$ is NH, and
$R^3$ is a cyano $C_{1-6}$ haloalkyl group or a cyano $C_{1-6}$ alkyl group, tautomers or pharmaceutically acceptable salts of the compounds or solvates thereof.

(14) The compounds according to (13), wherein $R^3$ is a 3-cyano-1,1,1-trifluoropropan-2-yl group, a 2-cyano-1,1,1-trifluoropropan-2-yl group, a 2-cyanoethyl group or a 1-cyanopropan-2-yl group, tautomers or pharmaceutically acceptable salts of the compounds or solvates thereof.

(15) The compounds according to any one of (11) to (14), wherein $A^3$ is a cyclohexanediyl group, tautomers or pharmaceutically acceptable salts of the compounds or solvates thereof.

(16) The compounds according to any one of (11) to (15), wherein $L^3$ is a methylene group, tautomers or pharmaceutically acceptable salts of the compounds or solvates thereof.

(17) Medicaments containing the compound as defined in any one of (1) to (16), tautomers or pharmaceutically acceptable salts of the compounds or solvates thereof, as an active ingredient.

In the present invention, the compounds of the present invention represented by the formula (I), the formula (II) or the formula (III) may be present in the form of tautomers or geometrical isomers which undergo endocyclic or exocyclic isomerization, mixtures of tautomers or geometric isomers or mixtures of thereof. When the compounds of the present invention have an asymmetric center, whether or not resulting from an isomerization, the compounds of the present invention may be in the form of resolved optical isomers or in the form of mixtures containing them in certain ratios. Further, when the compounds of the present invention have two or more asymmetric centers, the compounds of the present invention can be in the form of diastereomers due to optical isomerism about them.

The compounds of the present invention may be in the form of a mixture of all these isomers in certain ratios. For example, diastereomer can be separated by techniques well known to those skilled in the art such as fractional crystallization, and optical isomers can be obtained by techniques well known in the field of organic chemistry for this purpose.

The present invention covers pharmaceutically acceptable salts of the compounds of the present invention represented by the formula (I), the formula (II) or the formula (III).

The compounds of the present invention represented by the formula (I), the formula (II) or the formula (III) may be converted to pharmaceutically acceptable salts or may be liberated from the resulting salts, if necessary.

The pharmaceutically acceptable salts of the present invention may be, for example, salts with alkali metals (such as lithium, sodium and potassium), alkaline earth metals (such as magnesium and calcium), ammonium, organic bases, amino acids, inorganic acids (such as hydrochloric acid, hydrobromic acid, phosphoric acid and sulfuric acid) and organic acids (such as acetic acid, citric acid, maleic acid, fumaric acid, tartaric acid, benzenesulfonic acid, methanesulfonic acid and p-toluenesulfonic acid).

The compounds of the present invention represented by the formula (I), the formula (II) or the formula (III) or pharmaceutically acceptable salts thereof may be in the form of arbitrary crystals, depending on the production conditions. The present invention covers these crystals.

The compounds of the present invention represented by the formula (I), the formula (II) or the formula (III) or pharmaceutically acceptable salts thereof may be in the form of arbitrary hydrates or solvates with organic solvents such as acetone, ethanol, 1-propanol and 2-propanol, and the present invention covers these hydrates, solvates and their mixtures.

The present invention covers prodrugs of the compounds of the present invention represented by the formula (I), the formula (II) or the formula (III).

Prodrugs are derivatives of medicinal compounds having chemically or metabolically degradable groups and give pharmacologically active medicinal compounds upon solvolysis or under physiological conditions in vivo. Methods for selecting or producing appropriate prodrugs are disclosed in, for example, Design of Prodrugs (Elsevier, Amsterdam 1985).

In the present invention, in the case of a compound having a hydroxy group, prodrugs like acyloxy derivatives obtained by reacting the compound with appropriate acyl halides, appropriate acid anhydrides or appropriate haloalkyloxycarbonyl compounds may, for example, be mentioned. Structures particularly preferred as prodrugs include —O—COC$_2$H$_5$, CO(t-Bu), —O—COC$_{15}$H$_{31}$, —O—CO[m-(CO$_2$Na)—C$_6$H$_4$], —O—COCH$_2$CH$_2$CO$_2$Na, —OCOCH(NH$_2$)CH$_3$, —O—COCH$_2$N(CH$_3$)$_2$ or —O—CH$_2$OCOCH$_3$ or the like.

In the case of a compound having an amino group, prodrugs obtained by reacting the compound having an amino group with appropriate acid halides, appropriate mixed acid anhydrides or haloalkyloxycarbonyl compounds may, for example, be mentioned. Structures particularly preferred as prodrugs include —CO(CH$_2$)$_{20}$OCH$_3$, —COCH(NH$_2$)CH$_3$, —CH$_2$OCOCH$_3$ or the like.

The present invention is used when it is expected to improve pathology of diseases associated with JAK1, JAK2 and JAK3 separately or in combination. Among these diseases, rheumatoid arthritis is associated with JAK1 Among these diseases, JAK1- and JAK3-associated diseases are, in addition to rheumatoid arthritis, inflammatory or proliferative dermatoses such as psoriasis, atopic dermatitis, contact dermatitis, eczematoid dermatitis, seborrheic dermatitis, lichen planus, pemphigus, pemphigoid, epidermolysis bullosa, hives, angioedema, angiitis, erythema, dermal eosinophilia, lupus erythematosus, acne and alopecia areata, immune-mediated dermatoses, reversible airway obstruction, mucitis and angitis.

In addition, asthma, Alzheimer disease, atherosclerosis, cancer, leukemia, rejection of organ or tissue grafts (such as heart, kidney, liver, bone marrow, skin, horn, lung, pancreas, islet, small intestine, extremities, muscles, nerves, intervertebral disks, trachea, myoblasts and cartilage), graft-versus-host reaction after bone marrow transplantation and autoimmune diseases such as rheumatic disease, systemic lupus erythematosus (SLE), Hashimoto's disease, multiple sclerosis, myasthenia gravis, type I diabetes and diabetic complications are mentioned.

Among these diseases, JAK1- and JAK2-associated diseases are cancer, leukemia, chronic myeloproliferative disorders and myelodysplastic syndrome.

As an application of the present invention, treatment, prevention or improvement of the above-mentioned diseases may be mentioned, but there is no restriction.

The compounds of the present invention can be synthesized by the processes mentioned later, but the production of the compounds of the present invention is not restricted to these general examples.

The compounds of the present invention can usually be purified by column chromatography, thin layer chromatography, high performance liquid chromatography (HPLC) or high performance liquid chromatography-mass spectrometry (LC-MS) and, if necessary, they may be obtained with high purity by recrystallization or washing with solvents.

In general, in the production of the compounds of the present invention, any solvents that are stable and inert under the reaction conditions and do not hinder the reactions may be used without any particular restrictions, and for example, sulfoxide solvents (such as dimethyl sulfoxide), amide solvents (such as N,N-dimethylformamide or N,N-dimethylacetamide), ether solvents (such as ethyl ether, 1,2-dimethoxyethane, tetrahydrofuran, 1,4-dioxane or cyclopentyl methyl ether), halogenated solvents (such as dichloromethane, chloroform or 1,2-dichloroethane), nitrile solvents (such as acetonitrile or propionitrile), aromatic hydrocarbon solvents (such as benzene or toluene), aliphatic hydrocarbon solvents (such as hexane or heptane), ester solvents (such as ethyl acetate), alcohol solvents (such as methanol, ethanol, 1-propanol, 2-propanol or ethylene glycol) and water may be mentioned. The reactions may be carried out in an arbitrary mixture of solvents mentioned above or in the absence of a solvent.

The production of the compounds of the present invention may be carried out at ordinary pressure, under pressure, under reduced pressure or with microwave irradiation.

In general, in the production of the compounds of the present invention, the reaction temperature is chosen appropriately within the range of from −78° C. to the boiling point of the solvent used for the reaction.

As acids generally used in the production of the compounds of the present invention, for example, organic acids (such as acetic acid, trifluoroacetic acid or p-toluenesulfonic acid) and inorganic acids (such as sulfuric acid or hydrochloric acid) may be mentioned.

As bases generally used in the production of the compounds of the present invention, for example, organic metal compounds (such as n-butyllithium, s-butyllithium, lithium-diisopropylamide or isopropylmagnesium bromide), organic bases (such as triethylamine, N,N-diisopropylethylamine or N,N-dimethylaminopyridine) or inorganic bases (such as sodium carbonate, potassium carbonate, cesium carbonate, sodium hydroxide, potassium hydroxide or sodium hydride) may be mentioned.

General processes for production of the compounds of the present invention are shown below, and the formulae of the intermediate and the end product in each step therein conceptually cover their protected derivatives, too.

Herein, protected derivatives are defined as compounds which can be converted to the desired product, if necessary, through hydrolysis, reduction, oxidation, alkylation or the like and include compounds protected with protective groups acceptable to organic synthetic chemistry.

Protection and deprotection may be carried out by protection and deprotection reactions using generally known protective groups (for example, by referring to Protective Groups in Organic Synthesis, Fourth edition, T. W. Greene, John Wiley & Sons Inc. (2006)).

Hydrolysis, reduction and oxidation may be carried out by generally known functional group conversions (for example, by referring to Comprehensive Organic Transformations, Second Edition, R. C. Larock, Wiley-VCH (1999)).

The compounds of the present invention represented by the formula (I), the formula (II) and the formula (III) can be produced, for example, through the following scheme (2) or (3).

According to the scheme (2), a compound (2)-2 can be obtained by treating a compound (2)-1 with an equivalent or excessive amount of an unit (1)-3 in the presence of a base such as N,N-disopropylethylamine in an appropriate solvent or in the absence of solvent at room temperature to a refluxing temperature.

A compound (2)-3 can be obtained by treating a compound (2)-2 with an equivalent or excessive amount of 1,1'-carbonyldiimidazole in the presence of a base such as N,N-diisopropylethylamine in an appropriate solvent or in the absence of solvent at room temperature to a refluxing temperature.

According to the following scheme (3), a compound (3)-2 can be obtained by treating a compound (3)-1 with an equivalent or excessive amount of a compound (4)-1 in an appropriate solvent at −78° C. to a refluxing temperature.

A compound (3)-3 can be obtained by treating a compound (3)-2 with an equivalent or excessive amount of a unit (1)-3 in the presence of a base such as tripotassium phosphate in an appropriate solvent or in the absence of solvent at room temperature to a refluxing temperature.

The unit (1)-3 used herein can be produced, for example, through the following scheme (1).

According to the following scheme (1), a compound (1)-2 can be obtained by treating a carboxylic acid (1) with an equivalent or excessive amount of diphenylphosphoryl azide in the presence of a base such as triethylamine in an appropriate solvent or in the absence of solvent at room temperature to a refluxing temperature and then treating with an equivalent or excessive amount of benzyl alcohol or tert-butyl alcohol and can be converted to a unit (1)-3 by an appropriate deprotection.

In the following schemes, $R^{pr}$ is a hydrogen atom or a protective group such as a Ts group, a TIPS group or a SEM group. When $R^{pr}$ is not a hydrogen atom, it can be converted to a hydrogen atom by an appropriate deprotection.

A is the same as $A^1$, $A^2$ or $A^3$ previously defined, and may, for example, be a cyclopropane-1,2-diyl group, a cyclobutane-1,3-diyl group, a cyclopentane-1,3-diyl group, a cyclohexane-1,4-diyl group, a cycloheptane-1,4-diyl group or the like.

L is the same as $L^1$, $L^2$ or $L^3$ previously defined, X is a single bond or the same as $X^1$ or $X^3$ previously defined, and R is the same as $R^1$, $R^2$ or $R^3$ previously defined.

$R^b$ is a benzyl group, a t-butyl group or the like.

Q is a hydrogen atom or a protective group such as a TMS group. When Q is not a hydrogen atom, it can be converted to a hydrogen atom by an appropriate deprotection.

T is a group generating a carbanion at a terminal alkyne such as lithium or magnesium bromide.

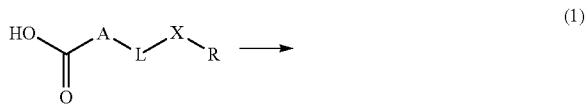

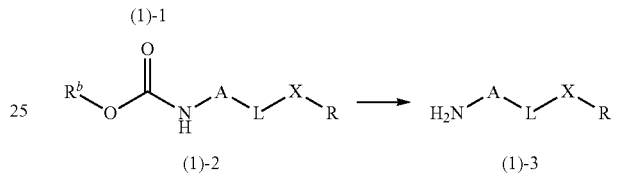

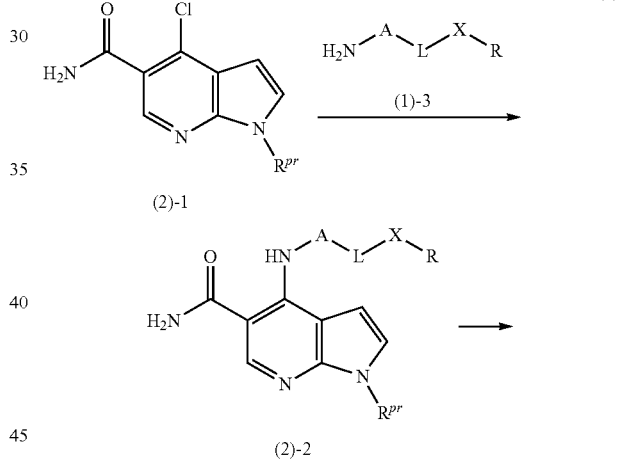

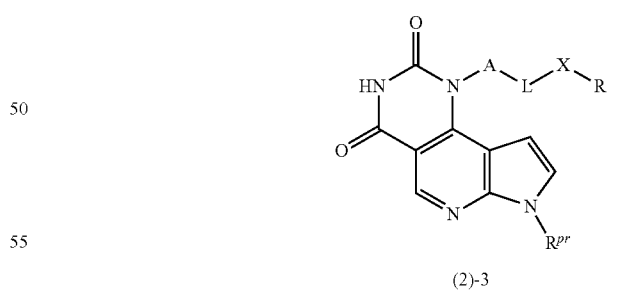

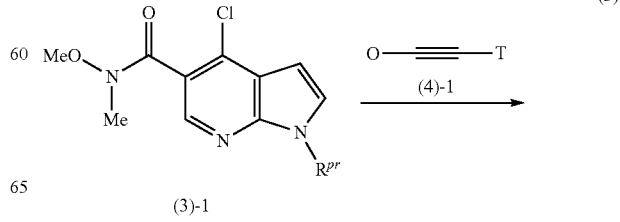

-continued (3)-2

(1)-3

(3)-3

Now, the present invention will be described in further detail with reference to Reference Synthetic Examples, Synthetic Examples, Pharmacological assay and Formulation Examples. However, it should be understood that the present invention is by no means restricted by these specific Examples.

In the Examples, "NMR" denotes nuclear magnetic resonance, "LC/MS" denotes high performance liquid chromatography-mass spectrometry, "(v/v)" means (volume/volume), "(v/v/v)" means (volume/volume/volume), "M" means mol/L. In the tables, "Rf" denotes Reference Synthetic Example, "Ex" denotes Synthetic Example, "Data" denotes physical property data, "Yield" denotes yield of a synthesized compound, "quant" denotes quantitative, and "min" denotes minute.

The $^1$H-NMR data show chemical shifts δ (unit: ppm) (splitting pattern, value of integral) measured at 300 MHz (with JNM-ECP300, manufactured by JEOL Ltd or JNM-ECX300, manufactured by JEOL Ltd) using tetramethylsilane as an internal standard, "s" denotes "singlet", "d" denotes "doublet", "t" denotes "triplet", "q" denotes "quartet", "quint" denotes quintet, "sextet" denotes sextet, "septet" denotes septet, "dd" denotes doublet of doublets, "dt" denotes doublet of triplets, "td" denotes triplet of doublets, "dq" denotes doublet of quartets, "qd" denotes quartet of doublets, "tt" denotes triplet of triplets, "ddd" denotes doublet of doublet of doublets, "m" denotes multiplet, "br" denotes broad, "J" denotes coupling constant, "CDCl$_3$" denotes deuterated chloroform, "CD$_3$OD" denotes deuterated methanol, and "DMSO-d$_6$" denotes deuterated dimethyl sulfoxide.

For purification by silica gel column chromatography, Hi-Flash (registered trademark) column manufactured by Yamazen Corporation, a silica gel 60 manufactured by Merck KGaA, Darmstadt, Germany or PSCQ60B manufactured by Fuji Silysia Chemical Ltd. was used unless otherwise noted.

For purification by silica gel thin layer chromatography, PLC plate manufactured by Merck KGaA, Darmstadt, Germany was used unless otherwise noted.

As a microwave reactor, Initiator sixty manufactured by Biotage was used.

The absolute configurations, if specified, are those of known compounds or those of derivatives from known compounds, or those measured by single-crystal X-ray structural analysis (with SMART APEX II ULTRA (manufactured by Bruker AXS), X ray: CuKα (50 kV, 24 mA), measurement temperature: −50° C.).

LC/MS spectra were measured by using ESI (electrospray ionization). "ESI$^+$" denotes ESI-positive mode, and "ESI$^-$" denotes ESI-negative mode.

LC/MS Measurement Condition 1:
Instrument: Waters Alliance
  Waters ZQ
Column: Waters SunFire C$_{18}$ (3.5 μm, 2.1×20 mm)
Column Temp.: 40° C.
Eluents: Liquid A: 0.1 wt % aqueous formic acid
  Liquid B: 0.1 wt % formic acid in acetonitrile
Elution: A mixture of Liquids A and B was flown at 0.4 mL/min while the mixing ratio was linearly changed from 90/10 (v/v) to 15/85 (v/v) over the first 3 minutes, and then the flow rate was linearly changed to 0.5 mL/min over 2 minutes at a constant mixing ratio of 15/85 (v/v). Then, the mixing ratio was linearly changed to 90/10 (v/v) over 0.5 minute and maintained at 90/10 (v/v) for 2.5 minutes.

LC/MS Measurement Condition 2:
Instrument: Waters AQUITY UPLC-PDA/CAD
  Thermo LTQ XL
Column: Waters AQUITY LIPLC BEH C$_{18}$ (1.7 μm, 2.1×50 mm)
Column Temp.: 40° C.
Eluents: Liquid A: 0.1 wt % aqueous formic acid
  Liquid B: 0.1 wt % formic acid in acetonitrile
Elution: A mixture of Liquids A and B was flown at 0.6 mL/min at a mixing ratio of 90/10 (v/v) for the first 0.5 minute, and then the mixing ratio was linearly changed to 10/90 (v/v) over 2.5 minutes and then maintained at 10/90 (v/v) for 0.7 minute. Then, the mixing ratio and the flow rate were linearly changed to 90/10 (v/v) and 0.8 mL/min, respectively, over 0.1 minute and maintained constant for 1 minute.

LC/MS Measurement Condition 3:
Instrument: Waters AQUITY UPLC-PDA/CAD
  Thermo LTQ XL
Column: Waters AQUITY UPLC BEH C$_{18}$ (1.7 μm, 2.1×50 mm)
Column Temp.: 40° C.
Eluents: Liquid A: 0.1 wt % aqueous formic acid
  Liquid B: 0.1 wt % formic acid in acetonitrile
Elution: A mixture of Liquids A and B was flown at 0.6 mL/min while the mixing ratio was linearly changed from 80/20 (v/v) to 0/100 (v/v) over 2.5 minutes, and the mixing ratio was maintained at 0/100 (v/v) for 1.2 minutes. Then, the mixing ratio and the flow rate were linearly changed to 80/20 (v/v) and 0.8 mL/min, respectively, over 0.1 minute and maintained constant for 1.0 minute.

LC/MS Measurement Condition 4:
Instrument: Waters AQUITY H-Class/PDA
  Waters SQ Detector 2
Column: Waters AQUITY UPLC BEH C18 (1.7 μm, 2.1×50 mm)
Column Temp.: 40° C.
Eluents: Liquid A: 0.1 wt % aqueous formic acid
  Liquid B: 0.1 wt % formic acid in acetonitrile
Elution: A mixture of Liquids A and B was flown at 0.6 mL/min while the mixing ratio was linearly changed from 90/10 (v/v) to 10/90 (v/v) over 3 minutes, and then the mixing ratio was maintained at 10/90 (v/v) for 0.7 minute. Then, the mixing ratio and the flow rate were linearly changed to 90/10 (v/v) and 0.8 mL/min, respectively, over 0.1 minute and maintained constant for 1.0 minute.

Reference Synthetic Example 1

Methyl trans-4{[(benzyloxy)carbonyl]amino}cyclohexanecarboxylate

Commercially available trans-4-(methoxycarbonyl)cyclohexanecarboxylic acid (157 g, 84.3 mmol) in toluene (160 mL) was stirred with triethylamine (35.0 mL, 253.0 mmol) at 110° C., and diphenylphosphoryl azide (20.0 mL, 92.7 mmol) was added dropwise over 30 minutes. After 3 hours of stirring at 110° C., benzyl alcohol (11.3 ml, 109.6 mmol) was added dropwise over 10 minutes, and the reaction solution was stirred for another 1 hour and 30 minutes. The reaction mixture was allowed to cool to room temperature, and after addition of 10 wt % aqueous citric acid, extracted with ethyl acetate. The organic layer was washed with saturated aqueous sodium hydrogen carbonate and with saturated aqueous sodium chloride, dried over anhydrous sodium sulfate and concentrated under reduced pressure. The residue was washed with a solvent mixture of hexane/ethyl acetate (=9/1 (v/v)) to give a mixture containing the title compound as a white solid (18.0 g),

Reference Synthetic Example 2 trans-4-{[(Benzyloxy)carbonyl]amino}cyclohexanecarboxylic acid

1 M aqueous sodium hydroxide (100 ml) was added to a solution of the mixture (18.0 g) contain rig methyl trans-4-{[(benzyloxy)carbonyl]amino}cyclohexanecarboxylate obtained in Reference Synthetic Example 1 in methanol (180 mL), and the resulting reaction mixture was stirred for 1 day and acidified with concentrated hydrochloric acid. The precipitated solid was washed with ethyl acetate and with water to give a mixture containing the title compound as a white solid (13.0 g). Further, the filtrate was extracted with ethyl acetate, and the organic layer was washed with saturated aqueous ammonium chloride, dried over anhydrous sodium sulfate and concentrated under reduced pressure to give a mixture containing the title compound as a white solid (6.7 g) The white solids were combined and used for in the next step without further purification.

Reference Synthetic Example 3

Benzyl [trans-4-(hydroxymethyl)cyclohexyl]carbamate

Boran-tetrahydrofuran complex (8.5 wt % in tetrahydrofuran, 30 mL) was added dropwise to a solution of trans-4-{[(benzyloxy)carbonyl]amino}cyclohexanecarboxylic acid (6.0 g) obtained in Reference Synthetic Example 2 in tetrahydrofuran (30 ml) under cooling with ice, and the resulting reaction mixture was stirred at room temperature for 1 day, and after addition of acetic acid, extracted with ethyl acetate. The organic layer was washed with saturated aqueous sodium hydrogen carbonate and with saturated aqueous sodium chloride, dried over anhydrous sodium sulfate and concentrated under reduced pressure. The resulting solid was washed with a solvent mixture of hexane/ethyl acetate (=10/1 (v/v)) to give a mixture containing the title compound as a white solid (6.0 g).

Reference Synthetic Example 4

Benzyl {trans-4-[(3,3,3-trifluoropropoxy)methyl]cyclohexyl}carbamate

A solution of benzyl [trans-4-(hydroxymethyl)cyclohexyl]carbamate (630 mg, 2.39 mmol) obtained in Reference Synthetic Example 3 in dichloromethane (5 mL) was stirred with 1,1,1-trifluoro-3-iodopropane (250 μL, 2.20 mmol), 2,6-di-tert-butylpyridine (500 μL, 2.27 mmol) and silver trifluoromethanesulfonate (500 mg, 1.99 mmol) for 5 hours and with 1,1,1-trifluoro-3-iodopropane (100 μL, 0.880 mmol), 2,6-di-tert-butylpyridine (200 μL, 0.909 mmol) and silver trifluoromethanesulfonate (200 mg, 0.797 mmol) for 1 day. After addition of saturated aqueous ammonium chloride, the reaction mixture was extracted with ethyl acetate. The organic layer was washed with saturated aqueous sodium hydrogen carbonate, dried over anhydrous sodium sulfate and concentrated under reduced pressure. The residue was purified by silica gel column chromatography (hexane/ethyl acetate=10/1→3/1 (v/v)) to give a mixture containing the title compound as a white amorphous (478 mg).

Reference Synthetic Example 5

Trans-4-[(3,3,3-Trifluoropropoxy)methyl]cyclohexanamine

A solution of the mixture (478 mg) containing benzyl {trans-4-[(3,3,3-trifluoropropoxy)methyl]cyclohexyl}carbamate obtained in Reference Synthetic Example 4 in methanol (5 mL) was stirred with 10 wt % palladium-carbon (50 wt % aq., 200 mg) under a hydrogen atmosphere for 2 hours and then filtered. The filter cake was washed with ethyl acetate, and the filtrate was concentrated under reduced pressure to give a mixture containing the title compound as a gray amorphous (308 mg).

Reference Synthetic Example 6

1-{trans-4-[(Benzylamino)methyl]cyclohexy}-7-{[2-(trimethylsily)ethoxy]methyl}-1H-pyrrolo[3',2':5,6]pyrido[4,3-d]pyrimidine-2,4(3H,7H)-dione A mixture of trans-4-(2,4-dioxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexanecarbaldehyde (300 mg, 0.678 mmol) obtained in accordance with Reference Synthetic Example[b] 168 in WO2013/024895 methanol (10 mL) and acetic acid (1 mL) was stirred with benzylamine (141 μL, 2.03 mmol) at room temperature for 1 hour and then stirred with 2-picoline borane (109 mg, 1.02 mmol) at room temperature for 1 day. After addition of water, the reaction solution was extracted with chloroform, and the organic layer was washed with saturated aqueous sodium chloride, dried over anhydrous sodium sulfate and concentrated under reduced pressure. The resulting residue was purified by silica gel column chromatography (chloroform/methanol=100/1 (WV)) to give the title compound as a white solid (274 mg, yield 76%).

Reference Synthetic Example 7

1-[trans-4-(Aminomethyl)cyclohexyl]-7-{[2-(trimethylsilyl)ethoxy]methyl}-1H-pyrrolo[3',2':5,6]pyrido[4,3-d]pyrimidine-2,4(3H,7H)-dione acetate A mixture of 1-{trans-4-[(benzylamino)methyl]cyclohexyl}-7-{[2-(trimethylsilyl) ethoxy]methyl}-1H-pyrrolo[3',2':5,6]pyrido[4,3-d]pyrimidin-2,4(3H,7H)-dione (270 mg, 0.506 mmol) obtained in Reference Synthetic Example 6, 5 wt % palladium-carbon (50 wt % aq., 27 mg), methanol (3 mL), tetrahydrofuran (3 mL) and acetic acid (0.1 mL) was stirred under a hydrogen atmosphere at room temperature for 1 day. The reaction mixture was filtered, and the filtrate was concentrated under reduced pressure. The residue was washed with acetic acid and hexane to give the title compound as a white solid (232 mg, yield 90%).

Reference Synthetic Example 8

3-({[trans-4-(2,4-Dioxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}amino)-4,4,4-trifluorobutanenitrile A solution of 1-[trans-4-(aminomethyl)cyclohexyl]-7-{[2-(trimethylsilyl)ethoxy]methyl}-1H-pyrrolo[3',2':5,6]pyrido[4,3-d]pyrimidine-2,4(3H,7H)-dione acetate (52.5 mg, 0.1 mmol) obtained in Reference Synthetic Example 7 in acetonitrile (1.2 mL) was stirred with 1,8-diazabicyclo[5.4.0]undec-7-ene (15.8 µL, 1.0 mmol) and 4,4,4-trifluorocrotononitrile (50.0 mg, 0.5 mmol) at room temperature for 3 days. After addition of water, the reaction mixture was extracted with ethyl acetate. The organic layer was washed with saturated aqueous sodium chloride, dried over anhydrous sodium sulfate and concentrated under reduced pressure. The resulting residue was purified by silica gel column chromatography (HiFlash (registered trademark) column amino type manufactured by Yamazen Corporation: hexane/ethyl acetate=2/1 (v/v)→ethyl acetate→ethyl acetate/methanol=10/1 (v/v)) to give the title compound as a light brown solid (25.2 mg, yield 43%).

Reference Synthetic Example 9

(R)-3-({[trans-4-(2,4-Dioxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}amino)-4,4,4-trifluorobutanenitrile 3-({[trans-4-(2,4-Dioxo-7-{[2-(trimethylsilyl)ethoxy]methyl}-2,3,4,7-tetrahydro-1H-pyrrolo[3',2':5,6]pyrido[4,3-d]pyrimidin-1-cyclohexyl]methyl}amino)-4,4,4-trifluorobutanenitrile (126.8 mg, 0.2 mmol) obtained in Reference Synthetic Example 8 was purified by silica gel column chromatography (chiral column for medium pressure; CHIRALFLASH (registered trademark) IA: hexane/ethanol=9/1→7/3 (v/v)), and the fraction eluted at a retention time of 49-58 minutes was concentrated to give the title compound as a light brown solid (35.4 mg, yield 28%).

Reference Synthetic Example 10

[trans-4-(2,4-Dioxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl 1H-imidazole-1-carboxylate A solution of 4-{[trans-4-(hydroxymethyl)cyclohexyl]amino}-1-{[2-(trimethylsilyl) ethoxy]methyl}-1H-pyrrolo[2,3-b]pyridine-6-carboxamide (6.03 g, 14.4 mmol) obtained in accordance with Reference Synthetic Example[b] 166 in WO2013/024895 and 1,1-carbonyldiimidazole (11.7 g, 72.0 mmol) in N,N-dimethylacetamide (30 mL) was stirred with N,N-diisopropylethylamine (30 mL) at 120° C. for 2 hours and 20 minutes. The reaction solution was allowed to cool to room temperature and extracted by adding ethyl acetate (150 mL), saturated aqueous ammonium chloride (30 mL) and water, and the aqueous layer was extracted with ethyl acetate. The resulting organic layers were combined, washed with saturated aqueous ammonium chloride three times and then with saturated aqueous sodium chloride, dried over anhydrous sodium sulfate and concentrated under reduced pressure. The residue was filtered, and the collected solid was washed with hexane and dried under reduced pressure to give the title compound as a pale yellow solid (7.56 g, yield 97%).

Reference Synthetic Example 11

1-[trans-4-(Hydroxymethyl)cyclohexyl]-3,7-bis{[2-(trimethylsilyl)ethoxy]methyl}-1H-pyrrolo[3',2':5,6]pyrido[4,3-d]pyrimidine-2,4(3H,7H)-dione A solution of [trans-4-(2,4-dioxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl 1H-imidazole-1-carboxylate (7.56 g, 14.0 mmol) obtained in Reference Synthetic Example 10 in N,N-dimethylformamide (140 mL) was cooled to 0° C. and stirred with sodium hydride (55 wt % dispersion in mineral oil, 760 mg, 18.2 mmol) and [2-(chloromethoxy)ethyl]trimethylsilane (3.50 mL, 19.6 mmol) for 2 hours. After addition of water and saturated aqueous ammonium chloride, the reaction mixture was extracted with ethyl acetate. The organic layer was washed with saturated aqueous sodium chloride, dried over anhydrous sodium sulfate and concentrated under reduced pressure. The resulting residue was stirred with 1,4-dioxane (100 mL) and 1 M aqueous sodium hydroxide (30 mL) at room temperature for 2 hours. After addition of saturated aqueous ammonium chloride, the reaction mixture was extracted with ethyl acetate. The organic layer was washed with saturated aqueous sodium chloride, dried over anhydrous sodium sulfate and concentrated under reduced pressure. The residue was purified by silica gel column chromatography (hexane/ethyl acetate=70/30→47/53 (v/v)) to give the title compound as a yellow amorphous (5.87 g, yield 73%.

Reference Synthetic Example 12

1-{trans-4-[(3,3,3-Trifluoropropoxy)methyl]cyclohexyl}-3,7-bis{[2-(trimethylsilyl) ethoxy]methyl}-1H-pyrrolo[3',2':5,6]pyrido[4,3-d]pyrimidine-2,4(3H,7H)-dione A solution of 1-[trans-4-(hydroxymethyl)cyclohexyl]-3,7-bis{[2-(trimethylsilyl)ethoxy]methyl}-1H-pyrrolo[3',2':5,6]pyrido[4,3-d]pyrimidine-2,4(3H,7H)-dione (1.35 g, 2.35 mmol) obtained in Reference Synthetic Example 11 in dichloromethane (14 mL) was stirred with 1,1,1-trifluoro-3-iodopropane (1.34 mL, 11.8 mmol), 2,6-di-tert-butylpyridine (2.38 mL, 10.8 mmol) and silver trifluoromethanesulfonate (2.60 g, 10.1 mmol) for 113 hours. The reaction mixture was filtered, and the filtrate was extracted by adding chloroform and water. The resulting organic layer was dried over anhydrous sodium sulfate and concentrated under reduced pressure. The residue was purified by silica gel column chromatography three times (the first run: hexane/ethyl acetate=1/0→78/22 (v/v), the second run: hexane/ethyl acetate=1/0→4/1 (v/v), the third run: hexane/ethyl acetate=1/0→4/1 (v/v)) to give the title compound as a colorless amorphous (1.34 g, yield 85%).

Reference Synthetic Example 13

4-Chloro-N-methoxy-N-methyl-1-{[2-(trimethylsilyl)ethoxy]methyl}-1H-pyrrolo[2,3-b]pyridine-5-carboxamide A solution of 4-chloro-1-{[2-(trimethylsilyl)methyl]-1H-pyrrolo[2,3-b]pyridine-5-carboxylic acid (27.7 g, 84.8 mmol) obtained in accordance with Reference Synthetic Example[b] 87 in WO2013/024895 in dichloromethane (280 mL) was stirred with N,N-diisopropylethylamine (43.2 mL, 254 mmol) and N-hydroxybenzotriazole (4.58 g, 33.9 mmol) for 15 minutes and then stirred with N,O-dimethylhydroxylamine hydrochloride (24.8 g, 254 mmol) and 1-(3-dimethylaminopropyl)-3-ethylcarbodiimide hydrochloride (48.7 g, 254 mmol) at room temperature for 18 hours. After addition of water, the reaction mixture was extracted with chloroform twice. The organic layer was washed with saturated aqueous ammonium chloride, saturated aqueous sodium hydrogen carbonate and saturated aqueous sodium chloride, successively, dried over anhydrous sodium sulfate and concentrated under reduced pressure. The residue was purified by silica gel column chromatography (hexane/ethyl acetate=4/1→3/1 (v/v)) to give the title compound as a yellow oil (30.5 g, yield 97%).

Reference Synthetic Example 14

1-(4-Chloro-1-{[2-(trimethylsilyl)ethoxy]methyl}-1H-pyrrolo[2,3-b]pyridin-5-yl)prop-2-yn-1-one A solution of 4-chloro-N-methoxy-N-methyl-1-{[2-(trimethylsilyl)ethoxy]methyl}-1H-pyrrolo[2,3-b]pyridine-5-carboxamide (47.4 g, 128 mmol) obtained in Reference Synthetic Example 13 in tetrahydrofuran (150 mL) was stirred at 50-53° C., and after addition of ethynylmagnesium bromide (0.5 M tetrahydrofuran solution, 310 mL, 153 mmol) at a temperature of 46° C. or above, the reaction mixture was stirred for 3 hours, cooled by air to 30° C. and poured into ice −1 M hydrochloric acid (300-300 mL). The resulting mixture was stirred for 15 minutes and extracted with ethyl acetate. The resulting organic layer was washed with saturated aqueous sodium hydrogen carbonate and with saturated aqueous sodium chloride, dried over anhydrous sodium sulfate and concentrated under reduced pressure. The residue was filtered, and the collected solid was washed with hexane and dried under reduced pressure to give the title compound as a light brown solid (35.4 g, yield 83%).

Reference Synthetic Example 15

1-[trans-4-(Hydroxymethyl)cyclohexyl]-7-{[2-(trimethylsilyl)ethoxy]methyl}-1H-pyrrolo[2,3-h][1,6]naphthyridin-4(7H)-one To 1-(4-chloro-1-{[2-(trimethylsilyl)ethoxy]methyl}-1H-pyrrolo[2,3-b]pyridin-5-yl) prop-2-yn-1-one (35.3 g, 105 mmol) obtained in Reference Synthetic Example 14, (trans-4-aminocyclohexyl)methanol (16.4 g, 126 mmol) obtained in accordance with Reference Synthetic Example[b] 122 in WO2013/024895, tripotassium phosphate (44.7 g, 210 mmol) and dimethyl sulfoxide (175 mL) were added, and the reaction mixture was stirred at 100-110° C. for 2 hour and 30 minutes and allowed to cool to 50° C. Water was added to the reaction mixture, and the resulting solid was collected by filtration, washed with ethyl acetate and dried under reduced pressure to give the title compound as a pale yellow solid (32.1 g, yield 71%).

Reference Synthetic Example 16

Mixture of 1-(4-chloro-1-{[2-(trimethylsilyl)ethoxy]methyl}-1H-pyrrolo[2,3-b]pyridin-5-yl) pyop-2-yn-1-one and 1-(4-chloro-1-{[2-(trimethylsilyl)ethoxy]methyl}-1H-pyrrolo[2,3-b]pyridin-5-yl)-3-[methoxy(methyl)amino]prop-2-en-1-one Ethylmagnesium bromide (0.5 M tetrahydrofuran solution, 180 mL, 90.1 mmol) was stirred with a solution of 4-chloro-N-methoxy-N-methyl-1-{[2-(trimethylsilyl)ethoxy]methyl}-1H-pyrrolo[2,3-b]pyridine-5-carboxamide (27.8 g, 75.1 mmol) obtained in Reference Synthetic Example 13 in tetrahydrofuran (84.0 mL) at room temperature for 30 minutes, then heated to 50° C. and stirred for another 1 hour. The reaction mixture was cooled with ice, and after addition of saturated aqueous ammonium chloride, extracted with ethyl acetate. The organic layer was washed with saturated aqueous sodium chloride, dried over anhydrous sodium sulfate and concentrated under reduced pressure. The residue was dried at 50° C. under reduced pressure for 1 hour to give a brown oil containing the title compound (29.7 g). The brown oil was used for the next step without further purification.

Reference Synthetic Example 17

1-[trans-4-(Hydroxymethyl)cyclohexyl]-7-{[2-(trimethylsilyl)ethoxy]methyl}-1H-pyrrolo[2,3-h][1,6]naphthyridin-4(7H)-one A solution of the mixture (29.7 g) of 1-(4-chloro-1-{[2-(trimethylsilyl)ethoxy]methyl}-1H-pyrrolo[2,3-b]pyridin-5-yl)prop-2-yn-1-one and 1-(4-chloro-1-{[2-(trimethylsilyl)ethoxy]methyl}-1H-pyrrolo[2,3-b]pyridin-5-yl)-3-[methoxy(methyl)amino]prop-2-en-1-one obtained in Reference Synthetic Example 16 in dimethyl sulfoxide (300 mL) was stirred with tripotassium phosphate (31.9 g, 150 mmol) and (trans-4-aminocyclohexyl)methanol (11.6 g, 90.1 mmol) obtained in accordance with Reference Synthetic Example[b] 122 in WO2013/024895 at 90° C. for 3 hours and then at 110° C. for another 4 hours. The reaction mixture was allowed to cool to room temperature, and water and hexane were added. The precipitated solid was collected by filtration, washed with water, a solvent mixture of hexane/ethyl acetate (=1/1 (v/v)) and ethyl acetate successively and dried at 50° C. for 5 hours under reduced pressure to give the title compound as a light brown solid (24.1 g, yield 75%). (Alternative to Reference Synthetic Example 15)

Reference Synthetic Example 18 trans-4-(4-Oxo-7-{[2-(trimethylsilyl)ethoxy]methyl}-4,7-dihydro-1H-pyrrolo[2,3-h][1,6]naphthyridin-1-yl)cyclohexanecarbaldehyde A mixture of 1-[trans-4-(hydroxymethyl)cyclohexyl]-7-{[2-(trimethylsilyl) ethoxy]methyl}-1H-pyrrolo[2,3-h][1,6]

naphthyridin-4(7H)-one (1.07 g, 2.49 mmol) obtained in Reference Synthetic Example 15, dimethyl sulfoxide (21 mL) and dichloromethane (21 mL) was stirred with 2-iodoxybenzoic acid (1.05 g, 3.74 mmol) at 40° C. for 1 hour and 30 minutes. After addition of saturated aqueous sodium thiosulfate and saturated aqueous sodium hydrogen carbonate, the reaction mixture was extracted with ethyl acetate. The resulting organic layer was washed with saturated aqueous sodium chloride, dried over anhydrous sodium sulfate and concentrated under reduced pressure. The residue was purified by silica gel column chromatography (ethyl acetate→ethyl acetate/methanol=10/1 (v/v)) to give the title compound as a grey solid (827 mg, yield 78%).

Reference Synthetic Example 19

1-{trans-4-[(Benzylamino)methyl]cyclohexyl}-7-{[2-(trimethylsilyl)ethoxy]methyl}-1H-pyrrolo[2,3-h][1,6]naphthyridin-4(7H)-one Benzylamine (384 µL, 3.52 mmol) and 2-picoline borane (188 mg, 1.78 mmol) were added to a mixture of trans-4-(4-oxo-7-{[2-(trimethylsilyl)ethoxy]methyl}-4,7-dihydro-1H-pyrrolo[2,3-h][1,6]naphthyridin-1-yl)cyclohexanecarbaldehyde (500 mg, 1.17 mmol) obtained in Reference Synthetic Example 18, methanol (10 mL) and acetic acid (1.0 mL), and the resulting reaction mixture was stirred at room temperature for 1 day, and after addition of 1 M hydrochloric acid, extracted with ethyl acetate. The aqueous layer was mixed with 1 M aqueous sodium hydroxide and extracted with a solvent mixture of chloroform/2-propanol (=1/1 (v/v)). The organic layer was dried over anhydrous sodium sulfate and concentrated under reduced pressure. The resulting residue was purified by silica gel column chromatography (HiFlash (registered trademark) column amino type manufactured by Yamazen Corporation: hexane/ethyl acetate=1/1 (v/v)→ethyl acetate→ethyl acetate/methanol=10/1 (v/v)) to give the title compound as a pale yellow oil (390 mg, yield 65%).

Reference Synthetic Example 20

1-[trans-4-(Aminomethyl)cyclohexyl]-7-{[2-(trimethylsilyl)ethoxy]methyl}-1H-pyrrolo[2,3-h][1,6]naphthyridin-4(7H)-one A mixture of 1-{trans-4-[(benzylamino)methyl]cyclohexyl}-7-{[2-(trimethylsilyl) ethoxy]methyl}-1H-pyrrolo[2,3-h][1,6]naphthyridin-4(7H)-one (390 mg, 0.755 mmol) obtained in Reference Synthetic Example 19, methanol (5 mL), tetrahydrofuran (5 mL) and acetic acid (1 mL) was stirred with 10 wt % palladium-carbon (50 wt % eq., 59.0 mg) under a hydrogen atmosphere for 1 day and then filtered. The filter cake was washed with ethyl acetate, and the filtrate was concentrated under reduced pressure. The residue was purified by silica gel column chromatography (HiFlash (registered trademark) column amino type manufactured by Yamazen Corporation: ethyl acetate/methanol=10/1→chloroform/methanol=10/1 (v/v)) to give the title compound as a white solid (271 mg, yield 84%).

Reference Synthetic Example 21

4,4,4-Trifluoro-3-({[trans-4-(4-oxo-7-{[2-(trimethylsilyl)ethoxy]methyl}-4,7-dihydro-1H-pyrrolo[2,3-h][1,6]naphthyridin-1-yl)cyclohexyl]methyl}amino)butanenitrile The reactions in Reference Synthetic Example 8 were carried out in substantially the same manners except that 1-[trans-4-(aminomethyl)cyclohexyl]-7-{[2-(trimethylsilyl)ethoxy]methyl}-1H-pyrrolo[2,3-h][1,6]naphthyridin-4(7H)-one (50.0 mg, 0.117 mmol) obtained in Reference Synthetic Example 20 was used instead of 1-[trans-4-(aminomethyl)cyclohexyl]-7-{[2-(trimethylsilyl)ethoxy]methyl}-1H-pyrrolo[3',2':5,6]pyrido[4,3-d]pyrimidine-2,4(3H,7H)-dione acetate obtained in Reference Synthetic Example 7 to give the title compound as a brown oil (54.5 mg, yield 85%).

Reference Synthetic Example 22

(R)-4,4,4-Trifluoro-3-({[trans-4-(4-oxo-7-{[2-(trimethylsilyl)ethoxy]methyl}-4,7-dihydro-1H-pyrrolo[2,3-h][1,6]naphthyridin-1-yl)cyclohexyl]methyl}amino)butanenitrile 4,4,4-Trifluoro-3-({[trans-4-(4-oxo-7-{[2-(trimethylsilyl)ethoxy]methyl}-4,7-dihydro-1H-pyrrolo[2,3-h][1,6]naphthyridin-1-yl)cyclohexyl]methyl}amino)butanenitrile (129 mg, 0.236 mmol) obtained in Reference Synthetic Example 21 was purified by preparative high performance liquid chromatography (CHIRAL-PAK (registered trademark) IE 5 µm φ20×250 mm: hexane/ethanol/diethylamine=70/30/0.1 (v/v/v): flow rate 8 mL/min), and the fraction eluted at a retention time of 74.64 minutes containing a single optical isomer was concentrated to give the title compound as a light brown oil (53.9 mg, yield 42%).

Reference Synthetic Example 23

[trans-4-(4-Oxo-7-{[2-(trimethylsilyl)ethoxy]methyl}-4,7-dihydro-1H-pyrrolo[2,3-h][1,6]naphthyridin-1-yl)cyclohexyl]methyl methanesulfonate To a solution of 1-[trans-4-(hydroxymethyl)cyclohexyl]-7-{[2-(trimethylsilyl) ethoxy]methyl}-1H-pyrrolo[2,3-h][1,6]naphthyridin-4(7H)-one (1.50 g, 3.51 mmol) obtained in Reference Synthetic Example 15 in dichloromethane (35 mL) cooled to 0° C., triethylamine (1.47 mL, 10.5 mmol) was added, and then methanesulfonyl chloride (326 µL, 4.21 mmol) was gradually added dropwise. The reaction mixture was warmed to room temperature and stirred for 1 hour, cooled with ice, then mixed with water and extracted with ethyl acetate. The resulting organic layer was washed with saturated aqueous sodium chloride, dried over anhydrous sodium sulfate and concentrated under reduced pressure. The residue was purified by silica gel column chromatography (ethyl acetate→ethyl acetate/methanol=10/1 (v/v)) to give the title compound as a yellow amorphous (1.53 g, yield 86%).

Reference Synthetic Example 24

1-{trans-4-[(4-Methyl-1H-pyrazol-1-yl)methyl]cyclohexyl}-7-{[2-(trimethylsilyl) ethoxy]methyl}-1H-pyrrolo[2,3-h][1,6]naphthyridin-4(7H)-one To a solution of [trans-4-(4-oxo-7-{[2-(trimethylsilyl)ethoxy]methyl}-4,7-dihydro-1H-pyrrolo[2,3-h][1,6]naphthyridin-1-yl)cyclohexyl]methyl methanesulfonate (1.53 g, 3.03 mmol) obtained in Reference Synthetic Example 23 in N,N-dimethylformamide (30 mL) cooled to 0° C., 4-methyl-1H-pyrazole (500 µL, 6.06 mmol) was added, and then sodium hydride (55 wt % dispersion in mineral oil, 264 mg, 6.06 mmol) was gradually added. Then, the reaction mixture was warmed to room temperature, stirred for 12 hours and after addition of water under cooling with ice extracted with ethyl acetate. The resulting organic layer was washed with saturated aqueous sodium chloride, dried over anhydrous sodium sulfate and concentrated under reduced pressure. The residue was purified by silica gel column chromatography (ethyl acetate→ethyl acetate/methanol=10/1 (v/v)) to give the title compound as a colorless amorphous (1.33 g, yield 89%).

Reference Synthetic Example 25

1-{trans-4-[(2,2,2-Trifluoroethoxy)methyl]cyclohexyl}-7-{[2-(trimethylsilyl)ethoxy]methyl}-1H-pyrrolo[2,3-h][1,6]naphthyridin-4(7H)-one To a solution of [1-trans-4-(hydroxymethyl)cyclohexyl]-7-{[2-(trimethylsilyl) ethoxy]methyl}-1H-pyrrolo[2,3-h][1,6]naphthyridin-4(7H)-one (20 mg, 0.047 mmol) obtained in Reference Synthetic Example 15 in tetrahydrofuran (2 mL), 2,2,2-trifluoroethyl trifluoromethanesulfonate (50 µL, 0.35 mmol) and sodium hydride (55 wt % dispersion in mineral oil, 10 mg, 0.23 mmol) were added, and the reaction mixture was stirred at room temperature for 2 hours. Then, 2,2,2-trifluoroethyl trifluoromethanesulfonate (50 µL, 0.35 mmol) and sodium hydride (55 wt % dispersion mineral oil, 10 mg, 0.23 mmol) were added, and the reaction mixture was stirred at room temperature for another 2 hours. After addition of saturated aqueous sodium chloride, the reaction mixture was extracted with ethyl acetate. The resulting organic layer was dried over anhydrous sodium sulfate and concentrated under reduced pressure. The residue was purified by silica gel column chromatography (hexane/ethyl acetate=5/1→0/1→ethyl acetate/methanol=5/1 (v/v)) to give a mixture containing the title compound as a colorless oil (9.2 mg). The mixture containing the title compound was used for the next step without further purification.

Reference Synthetic Example 26

1-{trans-4-[(3,3,3-Trifluoropropoxy)methyl]cyclohexyl}-7-{[2-(trimethylsilyl) ethoxy]methyl}-1H-pyrrolo[2,3-h][1,6]naphthyridin-4(7H)-one A solution of 1-(4-chloro-1-{[2-(trimethylsilyl)ethoxy]methyl}-1H-pyrrolo[2,3-b]pyridin-5-yl)prop-2-yn-1-one (279 mg, 0.83 mmol) obtained in Reference Synthetic Example 14 in dimethyl sulfoxide (175 mL) was stirred with trans-4-[(3,3,3-trifluoropropoxy)methyl]cyclohexanamine (255 mg, 1.00 mmol) obtained in Reference Synthetic Example 5 and tripotassium phosphate (528 mg, 2.49 mmol) at 100° C. for 1 hour and then with trans-4-[(3,3,3-trifluoropropoxy)methyl]cyclohexanamine (51 mg, 0.2 mmol) at 100° C. for 2 hours. After addition water, the reaction mixture was extracted with ethyl acetate. The resulting organic layer was dried over anhydrous sodium sulfate and concentrated under reduced pressure. The resulting reddish oil (550 mg) containing the title compound was dissolved in methanol (5.5 mL) and stirred with 5 wt % palladium-cartoon (50 wt % aq., 100 mg) under a hydrogen atmosphere at room temperature for 22 hours. The reaction mixture was filtered, and the filtrate was concentrated under reduced pressure. The residue was purified by silica gel column chromatography (hexane/ethyl acetate=2/1→1/1→0/1 (v/v)) to give the title compound as a pale yellow oil (323 mg, yield 74%).

Reference Synthetic Example 27

4,4,4-Trifluoro-3-{[trans-4-(4-oxo-7-{[2-(trimethylsilyl)ethoxy]methyl}-4,7-dihydro-1H-pyrrolo[2,3-h][1,6]naphthyridin-1-yl)cyclohexyl]methoxy}butanenitrile A solution of 1-[trans-4-(hydroxymethyl)cyclohexyl]-7-{[2-(trimethylsilyl) ethoxy]methyl}-1H-pyrrolo[2,3-h][1,6]naphthyridin-4(7H)-one (14.5 g, 33.9 mmol) obtained in Reference Synthetic Example 15 in dichloromethane (290 mL) was stirred with 1,8-diazabicyclo[5.4.0]undec-7-ene (20.3 mL, 135 mmol) at 40° C. for 1 hour. The reaction mixture was cooled to room temperature and stirred with 4,4,4-trifluorocrotononitrile (7.13 mL, 67.7 mmol) at 30° C. for another 5 hours. After addition of ethyl acetate, the reaction mixture was concentrated under reduced pressure, and after addition of 10 wt % aqueous citric acid, extracted with ethyl acetate. The resulting organic layer was washed with saturated aqueous ammonium chloride and saturated aqueous sodium chloride successively, dried over anhydrous sodium sulfate and concentrated under reduced pressure. The residue was purified by silica gel column chromatography (HiFlash (registered trademark) column manufactured by Yamazen Corporation: ethyl acetate/hexane=1/1→2/1→1/0 (v/v), then ethyl acetate/methanol=35/1 (v/v)) twice. The resulting solid was further purified by silica gel column chromatography (PSQ60B manufactured by Fuji Silysia Chemical Ltd.: ethyl acetate/hexane=1/1→2/1→1/0 (v/v)) to give the title compound as a yellow 15.7 g, yield 85%).

Reference Synthetic Example 28

Mixture of 1-(4-chloro-1-{[2-(trimethylsilyl)ethoxy]methyl}-1H-pyrrolo[2,3-b]pyridin-5-yl)-3-(trimethylsilyl) prop-2-yn-1-one and 1-(4-chloro-1-{[2-(trimethylsilyl)ethoxy]methyl}-1H-pyrrolo[2,3-b]pyridin-5-yl)prop-2-yn-1-one n-Butyllithium (1.5 M normal hexane solution, 1.1 mL, 1.67 mmol) was added dropwise to a solution of trimethylsilylacetylene (0.26 mL, 1.83 mmol) in tetrahydrofuran (2.8 mL) at −15° C., and the reaction solution was stirred for 15 minutes. Then, a solution of 4-chloro-N-methoxy-N-methyl-1-{[2-(trimethylsilyl)ethoxy]methyl}-1H-pyrrolo[2,3-b]pyridine-5-carboxamide (564 mg, 1.52 mmol) obtained in Reference Synthetic Example 13 in tetrahydrofuran (2.8 mL) was added at −15° C., and the reaction solution was stirred at 0° C. for 30 minutes, poured into a mixture of ice −1 M hydrochloric acid (10 g-10 mL), then stirred for 15 minutes and extracted with ethyl acetate. The resulting organic layer was dried over anhydrous sodium sulfate and concentrated under reduced pressure to give a mixture containing the title compounds as yellow oil (572 mg). The mixture containing the title compounds was used for the next step without further purification.

Reference Synthetic Example 29

1-[trans-4-(Hydroxymethyl)cyclohexyl]-7-{[2-(trimethylsilyl)ethoxy]methyl}-1H-pyrrolo[2,3-h][1,6]naphthyridin-4(7H)-one A solution of the mixture (572 mg) of 1-(4-chloro-1-{[2-(trimethylsilyl) ethoxy]methyl}-1H-pyrrolo[2,3-b]pyridin-5-yl)-3-(trimethylsilyl)prop-2-yn-1-one and 1-(4-chloro-1-{[2-(trimethylsilyl)ethoxy]methyl}-1H-pyrrolo[2,3-b]pyridin-5-yl) pyop-2-yn-1-one obtained in Reference Synthetic Example 28 in dimethyl sulfoxide (5 mL) was stirred with tripotassium phosphate (645 mg, 3.04 mmol) and (trans-4-aminocyclohexyl) methanol (237 mg, 1.82 mmol) obtained in accordance with Reference Synthetic Example[b] 122 in WO2013/024895 at 110° C. for 3 hours, and after addition of water, stirred at 50° C. for 2 hours. The precipitated solid was collected by filtration, washed with water and ethyl acetate successively and dried at 50° C. for 5 hours under reduced pressure to give the title compound as a pale yellow solid (340 mg, yield 52%). Separately, the washings were concentrated under reduced pressure, and the resulting brown solid was washed with ethyl acetate and dried at 50° C. for 3 hours to give the title compound as a pale yellow solid (68 mg, yield 10%). (Alternative to Reference Synthetic Example 15)

Synthetic Example 1

(R)-3-({[trans-4-(2,4-Dioxo-2,3,4,7-tetrahydro-1H-pyrrolo[3',2',5,6]pyrido[4,3-d]pyrimidin-1-yl)cyclohexyl]methyl}amino)-4,4,4-trifluorobutanenitrile A solution of (R)-3-({[trans-4-(2,4-dioxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}amino)-4,4,4-trifluorobutanenitrile (662 mg, 1.2 mmol) obtained in Reference Synthetic Example 9 in dichloromethane (13 mL) was stirred with trifluoroacetic acid (1.3 mL) at room temperature for 1 day and then stirred with trifluoroacetic acid (0.7 mL) at room temperature for another 3 hours. The reaction mixture was concentrated under reduced pressure to give a pale yellow oil containing (R)-4,4,4-trifluoro-3-[({trans-4-[7-(hydroxymethyl)-2,4-dioxo-2,3,4,7-tetrahydro-1H-pyrrolo[3',2':5,6]pyrido[4,3-d]pyrimidin-1-yl]cyclohexyl}methyl)amino]butanenitrile as an intermediate (LC/MS: measurement condition 2, retention time=1.88 min, LC/MS(ESI+) m/z; 465 [M+H]+). The intermediate was stirred with methanol (13 mL) and ethylenediamine (1.3 mL) at room temperature for 1 day. After addition of water and methanol, the reaction mixture was filtered. The collected solid was washed with methanol and dried under reduced pressure to give the title compound as a colorless solid (405 mg, yield 80%).

Synthetic Example 2

1-{trans-4-[(3,3,3-Trifluoropropoxy)methyl]cyclohexyl}-1H-pyrrolo[3',2':5,6]pyrido[4,3-d]pyrimidine-2,4(3H,7H)-dione The reactions in Synthetic Example 1 were carried out in substantially the same manners except that 1-{trans-4-[(3,3,3-trifluoropropoxy)methyl]cyclohexyl}-3,7-bis{[2-(trimethylsilyl) ethoxy]methyl}-1H-pyrrolo[3',2':5,6]pyrido[4,3-d]pyrimidine-2,4(3H,7H)-dione (790 mg, 1.18 mmol) obtained in Reference Synthetic Example 12 was used instead of (R)-3-({[trans-4-(2,4-dioxo-7-{[2-(trimethylsilyl) ethoxy]methyl}-2,3,4,7-tetrahydro-1H-pyrrolo[3',2':5,6]pyrido[4,3-d]pyrimidin-1-yl)cyclohexyl]methyl}amino)-4,4,4-trifluorobutanenitrile obtained in Reference Synthetic Example 9, and that 3,7-bis(hydroxymethyl)-1-{trans-4-[(3,3,3-trifluoropropoxy)methyl]cyclohexyl}-1H-pyrrolo[3',2':5,6]pyrido[4,3-d]pyrimidine-2,4(3H,7H)-dione (LC/MS: measurement condition 3, retention time=1.31 min, LC/MS (ESI+) m/z; 471 [M+H]+) was obtained as an intermediate, and the reaction mixture was filtered. The collected solid was washed with ethyl acetate to give the title compound as a white solid (416 mg, yield 86%).

Synthetic Example 3

(R)-4,4,4-Trifluoro-3-({[trans-4-(4-oxo-4,7-dihydro-1H-pyrrolo[2,3-h][1,6]naphthyridin-1-yl)cyclohexyl]methyl}amino)butanenitrile The reactions in Synthetic Example 1 were carried out in substantially the same manners except that (R)-4,4,4-trifluoro-3-({[trans-4-(4-oxo-7-{[2-(trimethylsilyl) ethoxy]methyl}-4,7-dihydro-1H-pyrrolo[2,3-h][1,6]naphthyridin-1-yl)cyclohexyl]methyl}amino)butanenitrile (1.11 g, 1.85 mmol) obtained in Reference Synthetic Example 22 was used instead of (R)-3-({[trans-4-(2,4-dioxo-7-{[2-(trimethylsilyl) ethoxy]methyl}-2,3,4,7-tetrahydro-1H-pyrrolo[3',2':5,6]pyrido[4,3-d]pyrimidin-1-yl)cyclohexyl]methyl}amino)-4,4,4-trifluorobutanenitrile obtained in Reference Synthetic Example 9, and that (R)-4,4,4-trifluoro-3-[({trans-4-[7-(hydroxymethyl)-4-oxo-4,7-dihydro-1H-pyrrolo[2,3-h][1,6]naphthyridin-1-yl]cyclohexyl}methyl)amino]butanenitrile (LC/MS: measurement condition 4, retention time=1.76 min, LC/MS(ESI+) m/z; 448 [M+H]+) was obtained as an intermediate, and the reaction mixture was extracted by adding a solvent mixture of chloroform/isopropanol (=1/1 (v/v)) and water. The organic layer was washed with saturated aqueous sodium chloride, dried over anhydrous sodium sulfate and concentrated under reduced pressure. The residue was purified by silica gel column chromatography (chloroform/methanol=1/0→1/1 (v/v), followed by HiFlash (registered trademark) column amino type manufactured by Yamazen Corporation: ethyl acetate/methanol=1/0→10/1 (v/v)) to give the title compound as a white solid (634 mg, yield 82%).

Synthetic Example 4

1-{trans-4-[(4-Methyl-1H-pyrazol-1-yl)methyl]cyclohexyl}-1H-pyrrolo[2,3-h][1,6]naphthyridin-4(7H)-one The reactions in Synthetic Example 1 were carried out in substantially the same manners except that 1-{trans-4-[(4-methyl-1H-pyrazol-1-yl)methyl]cyclohexyl}-7-{[2-(trimethylsilyl) ethoxy]methyl}-1H-pyrrolo[2,3-h][1,6]naphthyridin-4(7H)-one (133 g 2.70 mmol) obtained in Reference Synthetic Example 24 was used instead of (R)-3-({[trans-4-(2,4-dioxo-7-{[2-(trimethylsilyl) ethoxy]methyl}-2,3,4,7-tetrahydro-1H-pyrrolo[3',2':5,6]pyrido[4,3-d]pyrimidin-1-yl)cyclohexyl]methyl}amino)-4,4,4-trifluorobutanenitrile obtained in Reference Synthetic Example 9, and that 7-(hydroxymethyl)-1-{trans-4-[(4-methyl-1H-pyrazol-1-yl)methyl]cyclohexyl}-1H-pyrrolo[2,3-h][1,6]naphthyridin-4(7H)-one (LC/MS: measurement condition 2, retention time=1.64 min, LC/MS(ESI+) m/z; 392 [M+H]+) was obtained as an intermediate. Then, the reaction mixture was extracted by adding ethyl acetate and water, and the organic layer was washed with saturated aqueous sodium chloride, dried over anhydrous sodium sulfate and concentrated under reduced pressure. The residue was purified by silica gel column chromatography (HiFlash (registered trademark) column amino type manufactured by Yamazen Corporation: ethyl acetate) twice. The resulting solid was washed with ethyl acetate to give the title compound as a white solid (521 mg, yield 53%).

Synthetic Example 5

1-{trans-4-[(2,2,2-Trifluoroethoxy)methyl]cyclohexyl}-1H-pyrrolo[2,3-h][1,6]naphthyridin-4(7H)-one The reactions in Synthetic Example 1 were carried out in substantially the same manners except that the mixture (9.2 mg) containing 1-{trans-4-[(2,2,2-trifluoroethoxy) methyl]cyclohexyl}-7-{[2-(trimethylsilyl)ethoxy]methyl}-1H-pyrrolo[2,3-h][1,6]naphthyridin-4(7H)-one (138 mg, 0.271 mmol) obtained in Reference Synthetic Example 25 was used instead of (R)-3-({[trans-4-(2,4-dioxo-7-{[2-(trimethylsilyl) ethoxy]methyl}-2,3,4,7-tetrahydro-1H-pyrrolo[3',2':5,6]pyrido[4,3-d]pyrimidin-1-yl)cyclohexyl]methyl}amino)-4,4,4-trifluorobutanenitrile obtained in Reference Synthetic Example 9, and that 7-(hydroxymethyl)-1-{trans-4-[(2,2,2-trifluoroethoxy)methyl]cyclohexyl}-1H-pyrrolo[2,3-h][1,6]naphthyridin-4(7H)-one (LC/MS: measurement condition 2, retention time=1.95 min, LC/MS(ESI+) m/z; 410 [M+H]+) was obtained as an intermediate. Then, the reaction mixture was concentrated under reduced pressure, and the residue was purified by silica gel thin layer chromatography (ethyl acetate/hexane=5/1 (v/v)) to give the title compound as a white solid (3.8 mg, yield 21% (two steps)).

Synthetic Example 6

1-{trans-4-[(3,3,3-Trifluoropropoxy)methyl]cyclohexyl}-1H-pyrrolo[2,3-h][1,6]naphthyridin-4(7H)-one The reactions in Synthetic Example 1 were carried out in substantially the same manners except that 1-{trans-4-[(3,3,3-trifluoropropoxy)methyl]cyclohexyl}-7-{[2-(trimethylsilyl) ethoxy]methyl}-1H-pyrrolo[2,3-h][1,6]naphthyridin-4(7H)-one (1.47 g, 2.80 mmol) obtained in Reference Synthetic Example 26 was used instead of (R)-3-({[trans-4-(2,4-dioxo-7-{[2-(trimethylsilyl)ethoxy]methyl}-2,3,4,7-tetrahydro-1H-pyrrolo[3',2':5,6]pyrido[4,3-d]pyrimidin-1-yl)cyclohexyl]methyl}amino)-4,4,4-trifluorobutanenitrile obtained in Reference Synthetic Example 9, and that 7-(hydroxymethyl)-1-{trans-4-[(3,3,3-trifluoropropoxy)methyl]cyclohexyl}-1H-pyrrolo[2,3-h][1,6]naphthyridin-4(7H)-one (LC/MS: measurement condition 2, retention time=1.94 min, LC/MS(ESI+) m/z, 424 [M+H]+) was obtained as an intermediate. Then, the reaction mixture was extracted by adding chloroform and water, and the organic layer was washed with saturated aqueous sodium chloride, dried over anhydrous sodium sulfate and concentrated under reduced pressure. The residue was purified by silica gel column chromatography (ethyl acetate/methanol=1/0→95/5 (v/v), followed by chloroform/methanol=95/5→20/80 (v/v)) to give the title compound as a white solid (1.09 g, yield 98%).

Synthetic Example 7

(R)-4,4,4-Trifluoro-3-{[trans-4-(4-oxo-4,7-dihydro-1H-pyrrolo[2,3-h][1,6]naphthyridin-1-yl)cyclohexyl]methoxy}butanenitrile 4,4,4-Trifluoro-3-{[trans-4-(4-oxo-7-{[2-(trimethylsilyl) ethoxy]methyl}-4,7-dihydro-1H-pyrrolo[2,3-h][1,6]naphthyridin-1-yl)cyclohexyl]methoxy}butanenitrile (1.29 g, 2.35 mmol) obtained in Reference Synthetic Example 27 was purified by preparative high performance liquid chromatography (CHIRALPAK (registered trademark) IB 5 μm φ20×250 mm: hexane/ethanol=80/20→50/50 (v/v): flow rate 12 mL/min), and the fraction containing a single optically active isomer eluted at a retention time of 27.49 minutes was concentrated to give (R)-4,4,4-trifluoro-3-{[trans-4-(4-oxo-7-{[2-(trimethylsilyl) ethoxy]methyl}-4,7-dihydro-1H-pyrrolo[2,3-h][1,6]naphthyridin-1-yl)cyclohexyl]methoxy}butanenitrile (490 mg). Then, the reactions in Synthetic Example 1 were carried out in substantially the same manners except that (R)-4,4,4-trifluoro-3-{[trans-4-(4-oxo-7-{[2-(trimethylsilyl)ethoxy]methyl}-4,7-dihydro-1H-pyrrolo[2,3-h][1,6]naphthyridin-1-yl)cyclohexyl]methoxy}butanenitrile (490 mg, 0.893 mmol) obtained above was used instead of (R)-3-({[trans-4-(2,4-dioxo-7-{[2-(trimethylsilyl) ethoxy]methyl}-2,3,4,7-tetrahydro-1H-pyrrolo[3',2':5,6]pyrido[4,3-d]pyrimidin-1-yl)cyclohexyl]methyl}amino)-4,4,4-trifluorobutanenitrile obtained in Reference Synthetic Example 9, and that (R)-4,4,4-trifluoro-3-({trans-4-[7-(hydroxymethyl)-4-oxo-4,7-dihydro-1H-pyrrolo[2,3-h][1,6]naphthyridin-1-yl]Cyclohexyl}methoxy)butanenitrile (LC/MS: measurement condition 4, retention time=1.92 min, LC/MS(ESI+) m/z; 449 [M+H]+) was obtained as an intermediate. Then, the reaction mixture was extracted by adding ethyl acetate and water, and the organic layer was washed with saturated aqueous sodium chloride and concentrated under reduced pressure. The residue was purified by silica gel column chromatography (HiFlash (registered trademark) column amino type manufactured by Yamazen Corporation: ethyl acetate/methanol=1/0→92/8 (v/v)) to give the title compound as a white solid (299 mg, yield 30% (two steps)).

The structures of the respective compounds obtained in Reference Synthetic Example are shown below.

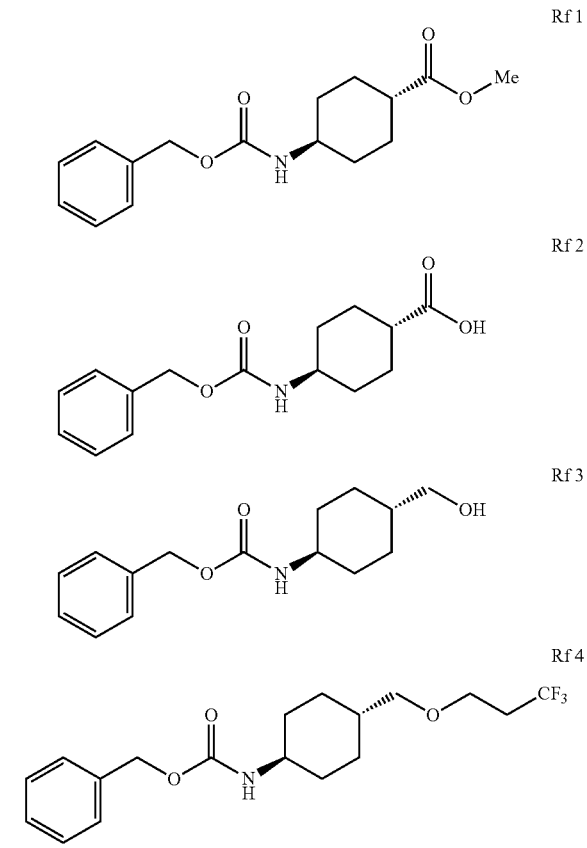

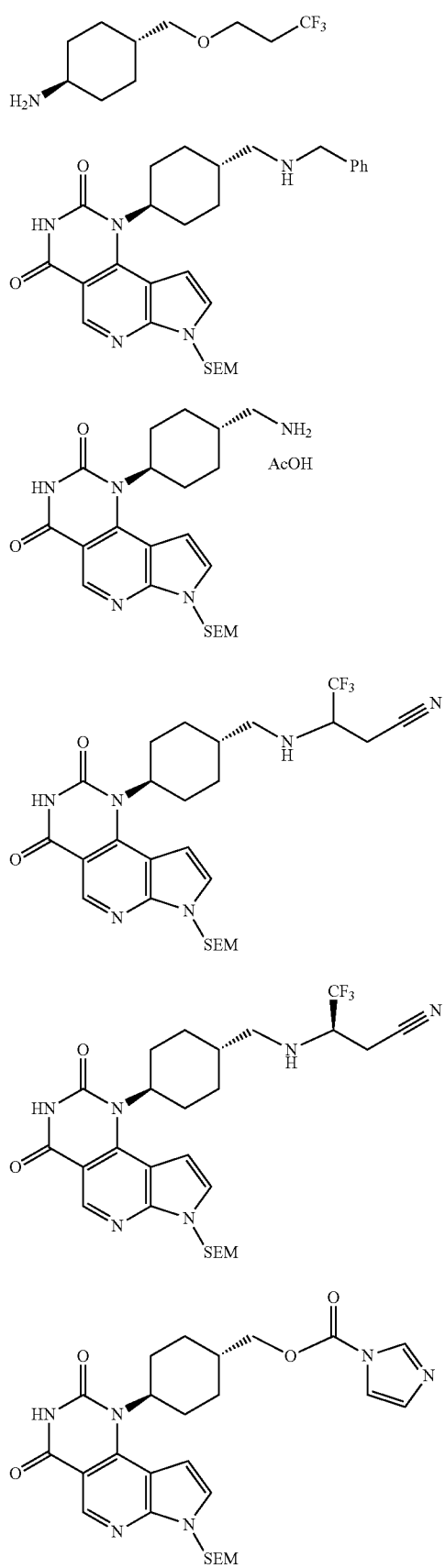
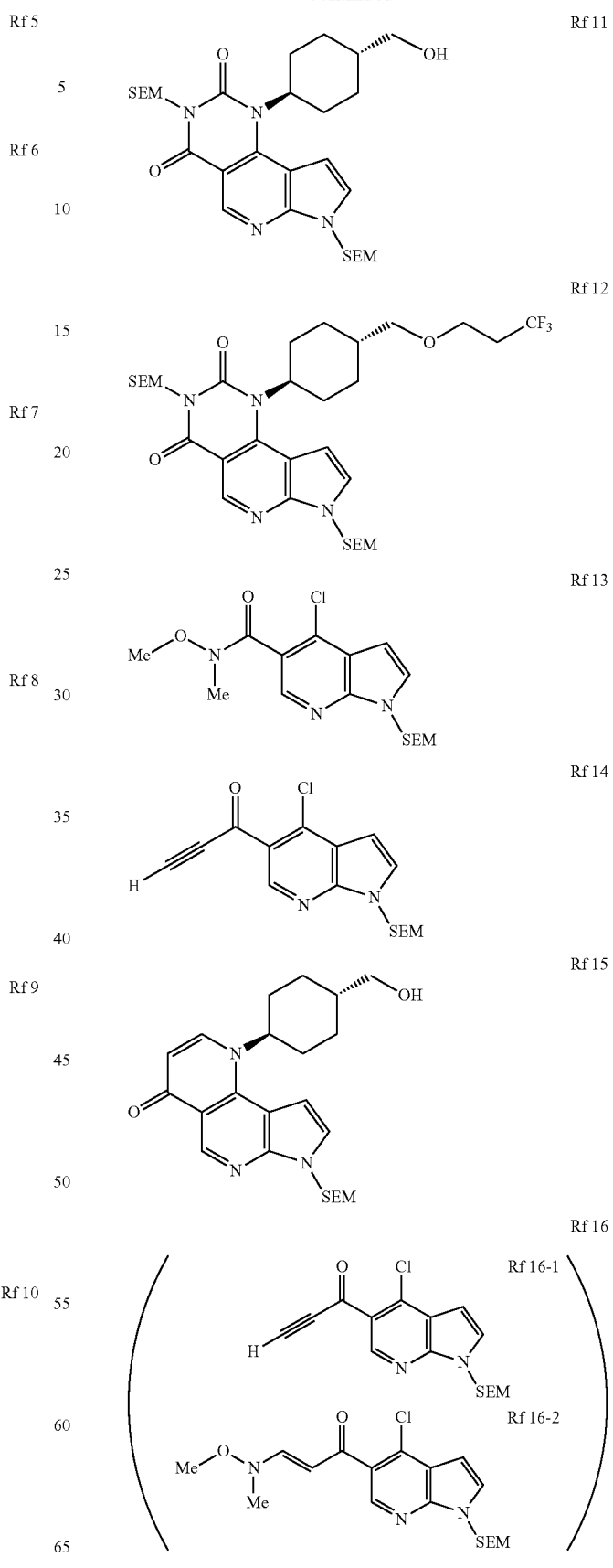

-continued
Rf 17
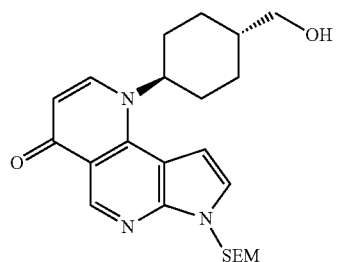
Rf 18
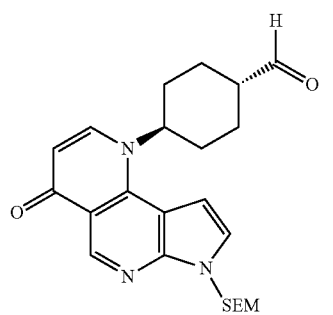
Rf 19
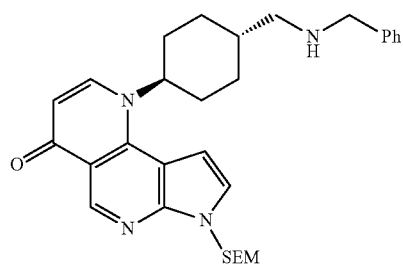
Rf 20
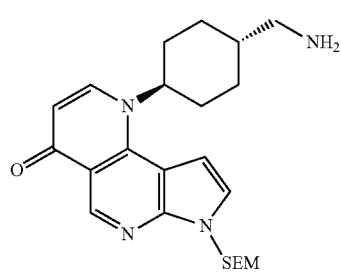
Rf 21
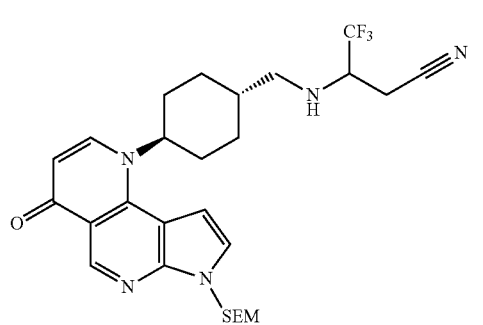
-continued
Rf 22
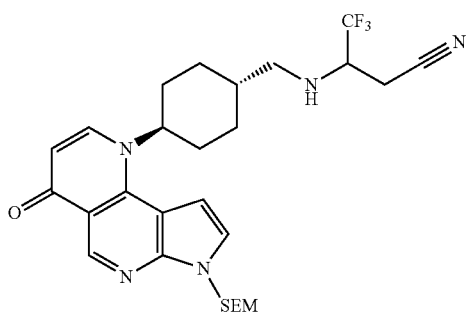
Rf 23
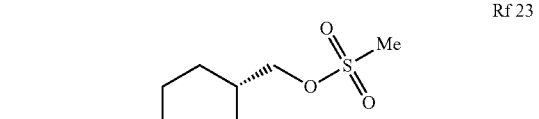
Rf 24
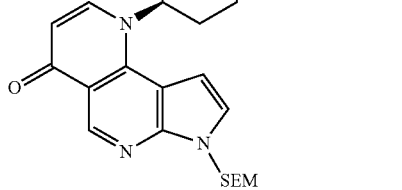
Rf 25
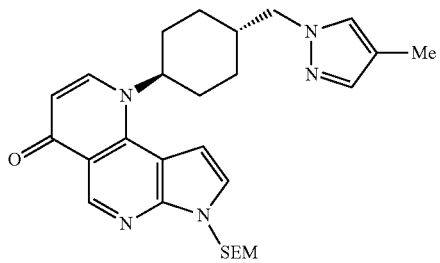
Rf 26
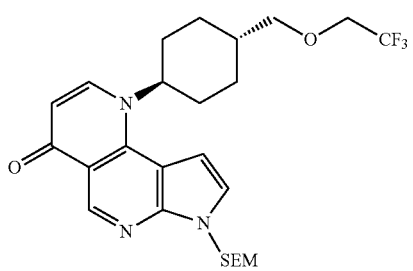
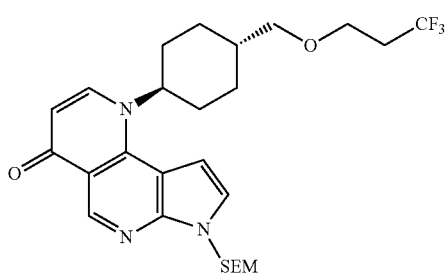

Rf 27
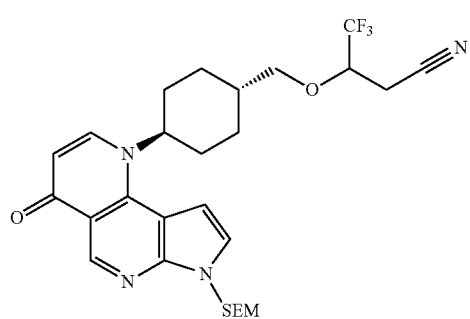
Ex 2
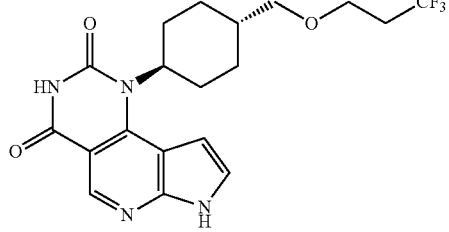
Rf 28
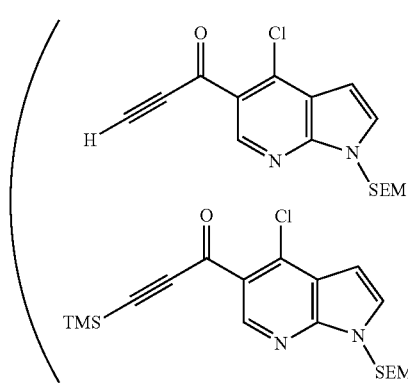
Ex 3
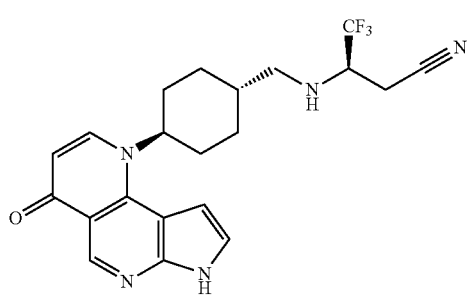
Ex 4
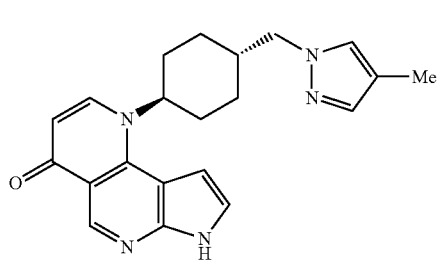
Ex 5
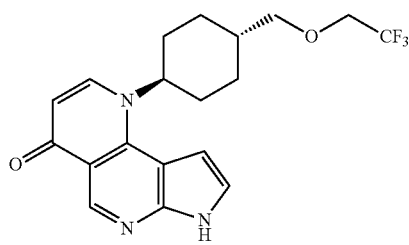
Rf 29
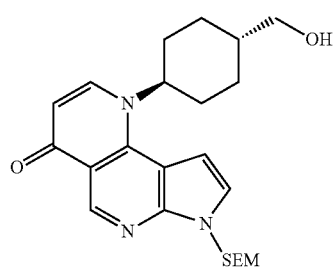
Ex 6
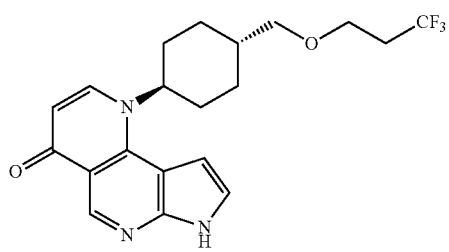
The structures of the respective compounds obtained in Synthetic Example are shown below.
Ex 1
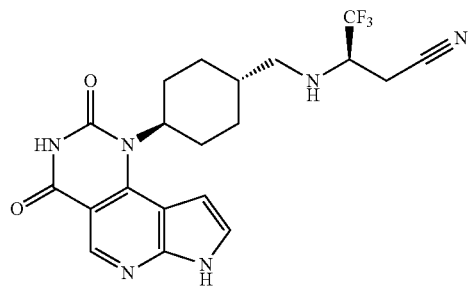
Ex 7
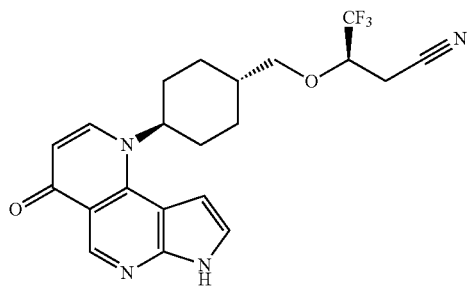

The physical property data on the compounds obtained the Reference Synthetic Examples and Synthetic Examples are shown below.

Rf1
LC/MS: measurement condition 2, retention time=2.25 min
LC/MS(ESI$^+$) m/z; 292 [M+H]$^+$ Rf2
LC/MS: measurement condition 2, retention time=1.92 min
LC/MS(ESI$^+$) m/z; 278 [M+H]$^+$ Rf3
LC/MS: measurement condition 2, retention time=1.93 min
LC/MS(ESI$^+$) m/z; 264 [M+H]$^+$ Rf4
LC/MS: measurement condition 2, retention time=2.66 min
LC/MS(ESI$^+$) m/z; 360 [M+H]$^+$ Rf5
LC/MS: measurement condition 2, retention time=1.29 min
LC/MS(ESI$^+$) m/z; 226 [M+H]$^+$ Rf8
$^1$H-NMR (CDCl$_3$) δ: 0.00 (s, 9H), 0.98 (t, J=8.2 Hz, 2H), 1.09-1.29 (m, 2H), 1.36-1.87 (m, 2H), 1.94-2.19 (m, 4H), 2.61 (d, J=6.5 Hz, 2H), 2.68-2.88 (m, 2H), 3.60 (t, J=8.4 Hz, 2H), 3.86 (s, 2H), 4.66-4.81 (m, 1H), 5.78 (s, 2H), 6.73 (d, J=3.7 Hz, 1H), 7.36-7.41 (m, 5H), 7.46 (d, J=3.7 Hz, 1H), 9.09 (s, 1H).

Rf7
$^1$H-NMR (DMSO-d$_6$) δ: −0.07 (s, 9H), 0.84 (t, J=8.0 Hz, 2H), 1.05-1.21 (m, 2H), 1.27-1.45 (m, 1H), 1.88-1.97 (m, 4H), 2.35-2.69 (m, 4H), 3.54 (t, J=8.2 Hz, 2H), 4.51-4.68 (m, 1H), 5.69 (s, 2H), 6.69 (d, J=3.7 Hz, 1H), 7.79 (d, J=3.7 Hz, 1H), 8.79 (s, 1H).

Rf8
$^1$H-NMR (DMSO-d$_6$) δ: −0.07 (s, 9H), 0.84 (t, J=8.0 Hz, 2H), 1.05-1.21 (m, 2H), 1.37-1.52 (m, 1H), 1.86-2.03 (m, 4H), 2.51-2.65 (m, 2H), 2.82 (dd, J=16.8, 8.2 Hz, 2H), 2.92 (dd, J=16.8, 5.3 Hz, 2H), 3.54 (t, J=8.2 Hz, 2H), 3.67-3.80 (m, 1H), 4.54-4.67 (m, 1H), 5.69 (s, 2H), 6.69 (d, J=4.1 Hz, 1H), 7.79 (d, J=4.1 Hz, 1H), 8.79 (s, 1H), 11.53 (br s, 1H).
LC/MS: measurement condition 1, retention time=4.59 min
LC/MS(ESI$^+$) m/z; 565 [M+H]$^+$
LC/MS(ESI$^+$) m/z; 563 [M−H]$^-$ Rf9
$^1$H-NMR (CDCl$_3$) δ: −0.05 (s, 9H), 0.87-0.98 (m, 2H), 1.10-1.28 (m, 3H), 1.96-2.06 (m, 2H), 2.07-2.20 (m, 2H), 2.56-2.89 (m, 6H), 3.39-3.48 (m, 1H), 3.52-3.59 (m, 2H), 4.64-4.76 (m, 1H), 5.73 (s, 2H) 6.69 (d, J=3.7 Hz, 1H), 7.43 (d, J=4.1 Hz, 1H), 8.06 (br s, 1H), 9.04 (s, 1H).

Rf10
$^1$H-NMR (CDCl$_3$) δ: −0.04 (s, 9H), 0.94 (t, J=8.3 Hz, 2H), 1.20-1.41 (m, 2H), 1.60-1.72 (m, 1H), 1.98-2.19 (m, 4H), 2.81 (q, J=11.9 Hz, 2H), 3.56 (t, J=8.3 Hz, 2H), 4.34 (d, J=6.3 Hz, 2H), 4.67-4.82 (m, 1H), 5.74 (s, 2H), 6.66 (d, J=4.2 Hz, 1H), 7.09-7.10 (m, 1H), 7.44-7.45 (m, 1H), 8.13 (br s, 1H), 8.16 (s, 1H), 9.05 (s, 1H).
LC/MS: measurement condition 2 retention time=2.47 min
LC/MS(ESI$^+$) m/z; 539 [M+H]$^+$ Rf11
$^1$H-NMR (CDCl$_3$) δ: −0.05 (s, 9H), 0.00 (s, 9H), 0.88-1.07 (m, 4H), 1.14-1.40 (m, 2H), 1.84-1.79 (br m, 1H), 1.94-2.15 (m, 4H), 2.70-2.89 (m, 2H), 3.51-3.65 (m, 4H), 3.73 (t, J=8.3 Hz, 2H), 4.62-4.77 (br m, 1H), 5.52 (s, 2H), 5.73 (s, 2H), 6.68 (d, J=3.6 Hz, 1H), 7.41 (d, J=3.6 Hz, 1H), 9.08 (s, 1H).
LC/MS: measurement condition 3, retention time=2.41 min
LG/MS(ESI$^+$) m/z: 575 [M+H]$^+$ Rf12
$^1$H-NMR (CDCl$_3$) δ: −0.05 (s, 9H), −0.01 (s, 9H), 0.87-1.03 (m, 2H), 1.16-1.30 (m, 4H), 1.71-1.84 (br m, 1H), 1.93-2.06 (m, 4H), 2.33-2.50 (m, 2H), 2.68-2.84 (m, 2H), 3.34 (d, J=6.0 Hz, 2H), 3.51-3.60 (m, 2H), 3.62-3.76 (m, 4H), 4.60-4.74 (br m, 1H), 5.51 (s, 2H), 5.72 (s, 2H), 6.67 (d, J=3.9 Hz, 1H), 7.40 (d, J=3.9 Hz, 1H), 9.07 (s, 1H).
LC/MS: measurement condition 3 retention time=2.85 min
LC/MS(ESI$^+$) m/z; 671 [M+H]$^+$ Rf13
$^1$H-NMR (CDCl$_3$) δ: −0.06 (s, 9H), 0.89-0.94 (m, 2H), 3.40-3.56 (m, 8H), 5.68 (s, 2H), 6.68 (d, J=3.6 Hz, 1H), 7.44 (d, J=3.6 Hz, 1H), 8.29 (s, 1H).
LC/MS: measurement condition 2 retention time=2.62 min
LC/MS(ESI$^+$) m/z; 370 [M+H]$^+$ Rf14
$^1$H-NMR (CD$_3$OD) δ: −0.05 (s, 9H), 0.91 (t, J=8.5 Hz, 2H), 3.51 (s, 3H), 3.54 (t, J=8.5 Hz, 2H), 5.69 (s, 2H), 6.78 (d, J=3.8 Hz, 1H), 7.44 (d, J=3.8 Hz, 1H), 9.14 (s, 1H).
LC/MS: measurement condition 2 retention time=2.93 min
LC/MS(ESI$^+$) m/z; 335 [M+H]$^+$ Rf15
LC/MS: measurement condition 2, retention time=2.14 min
LC/MS(ESI$^+$) m/z; 428 [M+H]$^+$ Rf16
Rf16-1
LC/MS: measurement condition 4, retention time=2.75 min
LC/MS(ESI$^+$) m/z; 335 [M+H]$^+$ Rf16-2
LC/MS: measurement condition 4, retention time=3.12 min
LC/MS(ESI$^+$) m/z; 396 [M+H]$^+$ Rf17
$^1$H-NMR (CDCl$_3$) δ: −0.06 (s, 9H), 0.90-0.96 (m, 2H), 1.41 (qd, J=12.3, 3.3 Hz, 2H), 1.66-1.71 (m, 1H), 1.86 (qd, J=12.3, 3.3 Hz, 2H), 2.12-2.17 (m, 2H), 2.30-2.33 (m, 2H), 3.53-3.59 (m, 2H), 3.63 (d, J=6.0 Hz, 2H), 4.93 (ft, J=12.3, 3.3 Hz, 1H), 5.80 (s, 2H), 6.43 (d, J=8.1 Hz, 1H), 6.78 (d, J=3.9 Hz, 1H), 7.43 (d, J=3.3 Hz, 1H), 7.76 (d, J=8.1 Hz, 1H), 9.40 (s, 1H).
LC/MS: measurement condition 2, retention time=2.16 min
LC/MS(ESI$^+$) m/z; 428 [M+H]$^+$ Rf18
$^1$H-NMR (CDCl$_3$) δ: −0.06 (s, 9H), 0.90-0.96 (m, 2H), 1.67 (qd, J=12.9, 3.3 Hz, 2H), 1.91 (qd, J=12.9, 3.3 Hz, 2H), 2.34-2.52 (m, 5H), 3.53-3.60 (m, 2H), 4.94 (tt, J=11.8, 2.9 Hz, 1H), 5.80 (s, 2H), 6.44 (d, J=8.1 Hz, 1H), 6.74 (d, J=3.7 Hz, 1H), 7.44 (d, J=3.7 Hz, 1H), 7.73 (d, J=8.1 Hz, 1H), 9.40 (s, 1H), 9.78 (s, 1H).
LC/MS: measurement condition 2, retention time=2.30 min
LC/MS(ESI$^+$) m/z; 426 [M+H]$^+$ Rf19
$^1$H-NMR (CDCl$_3$) δ: −0.06 (s, 9H), 0.88-0.96 (m, 2H), 1.33 (qd, J=12.6, 3.3 Hz, 2H), 1.57-1.71 (m, 1H), 1.84 (qd, J=12.6, 3.3 Hz, 2H), 2.11-2.21 (m, 2H), 2.23-2.33 (m, 2H), 2.62 (d, J=6.6 Hz, 2H), 3.52-3.59 (m, 2H), 3.83 (s, 2H), 4.91 (tt, J=11.9, 3.3 Hz, 1H), 5.80 (s, 2H), 6.43 (d, J=7.9 Hz, 1H), 6.77 (d, J=3.6 Hz, 1H), 7.32-7.37 (m, 5H), 7.42 (d, J=3.6 Hz, 1H), 7.76 (d, J=7.9 Hz, 1H), 9.40 (s, 1H).

LC/MS: measurement condition 1, retention time=3.19 min

LC/MS(ESI$^+$) m/z; 517 [M+H]$^+$

Rf20

$^1$H-NMR (CDCl$_3$) δ: −0.06 (s, 9H), 0.89-0.96 (m, 2H), 1.29-1.56 (m, 3H), 1.85 (qd, J=12.3, 2.9 Hz, 2H), 2.10-2.19 (m, 2H), 2.26-2.35 (m, 2H), 2.71 (d, J=6.1 Hz, 2H), 3.53-3.59 (m, 2H), 4.92 (tt, J=11.9, 3.3 Hz, 1H), 5.79 (s, 2H), 6.42 (d, J=8.2 Hz, 1H), 6.77 (d, J=3.7 Hz, 1H), 7.42 (d, J=3.7 Hz, 1H), 7.75 (d, J=8.2 Hz, 1H), 9.40 (s, 1H).

LC/MS: measurement condition 1 retention time=2.89 min

LC/MS(ESI$^+$) m/z; 427 [M+H]$^+$

Rf21

$^1$H-NMR (CDCl$_3$) δ: −0.06 s, 9H), 0.90-0.96 (m, 2H), 1.33-1.46 (m, 3H), 1.53-1.63 (m, 1H), 1.78-1.93 (m, 2H), 2.14-2.23 (m, 2H), 2.27-2.36 (m, 2H), 2.58-2.96 (m, 4H), 3.40-3.51 (m, 1H), 3.53-3.60 (m, 2H), 4.88-4.99 (m, 1H), 5.80 (s, 2H), 6.44 (d, J=8.3 Hz, 1H), 6.77 (d, J=4.0 Hz, 1H), 7.43 (d, J=4.0 Hz, 1H), 7.75 (d, J=8.3 Hz, 1H), 9.41 (s, 1H).

LC/MS: measurement condition 1, retention time=4.40 min

LC/MS(ESI$^+$) m/z; 548 [M+H]$^+$

Rf22

$^1$H-NMR (CDCl$_3$) δ: −0.06 (s, 9H), 0.89-0.97 (m, 2H), 1.30-1.48 (m, 3H), 1.54-1.67 (m, 1H), 1.77-1.94 (m, 2H), 2.14-2.23 (m, 2H), 2.26-2.36 (m, 2H), 2.58-2.96 (m, 4H), 3.40-3.51 (m, 1H), 3.52-3.61 (m, 2H), 4.93 (tt, J=11.8, 2.9 Hz, 1H), 5.80 (s, 2H), 6.43 (d, J=8.1 Hz, 1H), 6.77 (d, J=3.7 Hz, 1H), 7.43 (d, J=3.7 Hz, 1H), 7.75 (d, J=8.1 Hz, 1H), 9.40 (s, 1H).

LC/MS: measurement condition 2, retention time=2.68 min

LC/MS(ESI$^+$) m/z; 548 [M+H]$^+$

Rf23

$^1$H-NMR (CDCl$_3$) δ: −0.06 (s, 9H), 0.93 (t, J=8.4 Hz, 2H), 1.41-1.56 (m, 2H), 1.82-1.97 (m, 3H), 2.15-2.20 (m, 2H), 2.32-2.36 (m, 2H), 3.07 (s, 3H), 3.56 (t, J=8.4 Hz, 2H), 4.18 (d, J=6.0 Hz, 2H), 4.94 (tt, J=12.0, 3.3 Hz, 1H), 5.80 (s, 2H), 6.43 (d, J=7.8 Hz, 1H), 6.73 (d, J=3.9 Hz, 1H), 7.43 (d, J=3.9 Hz, 1H), 7.72 (d, J=8.1 Hz, 1H), 9.39 (s, 1H).

LC/MS: measurement condition 4, retention time=2.42 min

LC/MS(ESI$^+$) m/z; 506 [M+H]$^+$

Rf24

$^1$H-NMR (CDCl$_3$) δ: −0.06 (s, 9H), 0.90-0.95 (m, 2H), 1.39 (qd, J=12.3, 2.4 Hz, 2H), 1.83 (qd, J=12.3, 3.0 Hz, 2H), 1.95-2.07 (m, 3H), 2.09 (s, 3H), 2.26-2.30 (m, 2H), 3.53-3.59 (m, 2H), 4.02 (d, J=6.9 Hz, 2H), 4.91 (tt, J=12.0, 3.0 Hz, 1H), 5.80 (s, 2H), 6.42 (d, J=8.1 Hz, 1H), 6.74 (d, J=3.9 Hz, 1H), 7.17 (s, 1H), 7.34 (s, 1H), 7.43 (d, J=3.9 Hz, 1H), 7.70 (d, J=8.1 Hz, 1H), 9.39 (s, 1H).

LC/MS: measurement condition 4, retention time=2.62 min

LC/MS(ESI$^+$) m/z; 492 [M+H]$^+$

Rf25

LC/MS: measurement condition 2, retention time=2.80 min

LC/MS(ESI$^+$) m/z; 510 [M+H]$^+$

Rf26

$^1$H-NMR (CDCl$_3$) δ: −0.05 (s, 9H), 0.93 (t, J=8.5 Hz, 2H), 1.33-1.45 (m, 2H), 1.76-1.91 (m, 3H), 2.11-2.15 (m, 2H), 2.27-2.31 (m, 2H), 2.43 (qt, J=10.5, 6.0 Hz, 2H), 3.39 (d, J=6.0 Hz, 2H), 3.56 (t, J=8.5 Hz, 2H), 3.68 (t, J=6.6 Hz, 2H), 4.88-4.96 (m, 1H), 5.81 (s, 2H), 6.43 (d, J=8.1 Hz, 1H), 6.78 (d, J=3.6 Hz, 1H), 7.44 (d, J=3.6 Hz, 1H), 7.76 (d, J=8.1 Hz, 1H), 9.41 (s, 1H).

Rf27

$^1$H-NMR (CDCl$_3$) δ: −0.06 (s, 9H), 0.93 (t, J=8.2 Hz, 2H), 1.37-1.57 (m, 2H), 1.78-1.95 (m, 3H), 2.12-2.23 (m, 2H), 2.26-2.37 (m, 2H), 2.77 (d, J=6.6 Hz, 2H), 3.56 (t, J=8.3 Hz, 2H), 3.65-3.76 (m, 1H), 3.77-3.87 (m, 1H), 4.01 (dt, J=6.0, 12.1 Hz, 1H), 4.85-4.99 (m, 1H), 5.80 (s, 2H), 6.43 (d, J=8.1 Hz, 1H), 6.77 (d, J=3.7 Hz, 1H), 7.43 (d, J=3.7 Hz, 1H), 7.74 (d, J=8.1 Hz, 1H), 9.40 (s, 1H).

Rf28

Rf28-1

LC/MS: measurement condition 2, retention time=2.93 min

LC/MS(ESI$^+$) m/z; 335 [M+H]$^+$

Rf28-2

LC/MS: measurement condition 2, retention time=3.45 min

LC/MS(ESI$^+$) m/z; 406 [M+H]$^+$

Rf29

$^1$H-NMR (CDCl$_3$) δ: −0.06 (s, 9H), 0.90-0.96 (m, 2H), 1.41 (qd, J=12.6, 3.3 Hz, 2H), 1.66-1.71 (m, 1H), 1.86 (qd, J=12.3, 3.3 Hz, 2H), 2.12-2.17 (m, 2H), 2.30-2.33 (m, 2H), 3.53-3.59 (m, 2H), 3.64 (d, J=6.0 Hz, 2H), 4.93 (tt, J=12.3, 3.3 Hz, 1H), 5.80 (s, 2H), 6.44 (d, J=8.1 Hz, 1H), 6.79 (d, J=3.6 Hz, 1H), 7.43 (d, J=3.6 Hz, 1H), 7.77 (d, J=8.1 Hz, 1H), 9.40 (s, 1H).

LC/MS: measurement condition 2, retention time=2.15 min

LC/MS(ESI$^+$) m/z; 428 [M+H]$^+$

Ex1

$^1$H-NMR (DMSO-d$_6$) δ: 1.00-1.21 (m, 2H), 1.34-1.52 (m, 1H), 1.80-2.07 (m, 4H), 2.48-2.69 (m, 4H), 2.72-2.98 (m, 2H), 3.63-3.81 (m, 1H), 4.55-4.72 (m, 1H), 6.62 (d, J=3.6 Hz, 1H), 7.59 (d, =3.6 Hz, 1H), 8.73 (s, 1H), 10.80 (br s, 1H).

LC/MS: measurement condition 2, retention time=1.91 min

LC/MS(ESI$^+$) m/z, 435 [M+H]$^+$

LC/MS(ESI$^-$) m/z; 433 [M+H]$^-$

Ex2

$^1$H-NMR (DMSO-d$_6$) δ: 1.16 (q, J=11.8 Hz, 2H), 1.52-1.68 (br m, 1H), 1.89 (d, J=10.2 Hz, 4H), 2.49-2.63 (m, 4H), 3.22-3.43 (m, 2H), 3.60 (t, J=6.0 Hz, 2H), 4.55-4.69 (t, J=12.0 Hz, 1H), 6.59 (d, J=3.6 Hz, 1H), 7.59 (d, J=3.6 Hz, 1H), 8.72 (s, 1H), 12.35 (br s, 1H).

LC/MS: measurement condition 3, retention time=1.30 min

LC/MS(ESI$^+$) m/z; 411 [M+H]$^+$

LC/MS(ESI$^-$) m/z; 409 [M−H]$^-$ $^1$H-NMR (DMSO-d$_6$) δ: 1.23-1.39 (m, 2H), 1.45-1.59 (m, 1H), 1.84-1.99 (m, 2H), 2.00-2.14 (m, 4H), 2.56-2.69 (m, 2H), 2.79-2.98 (m, 2H), 3.66-3.79 (m, 1H), 4.83-4.95 (m, 1H), 6.20 (d, J=8.1 Hz, 1H), 6.80 (dd, J=3.3, 1.8 Hz, 1H), 7.58 (t, J=3.3 Hz, 1H), 8.17 (d, J=8.1 Hz, 1H), 9.02 (s, 1H), 12.32 (s, 1H).

LC/MS: measurement condition 2, retention time=1.83 min

LC/MS(ESI$^+$) m/z; 418 [M+H]$^+$

LC/MS(ESI$^+$) m/z; 416 [M−H]$^-$

Ex4

$^1$H-NMR (CD$_3$OD) δ: 1.41-1.55 (m, 2H), 1.86-2.05 (m, 5H), 2.10 (s, 3H), 2.23-2.28 (m, 2H), 4.06 (d, J=7.2 Hz, 2H), 5.05-5.15 (m, 1H), 6.45 (d, J=7.8 Hz, 1H), 6.94 (d, J=3.6 Hz,

1H), 7.32 (s, 1H), 7.44 (s, 1H), 7.56 (d, J=3.6 Hz, 1H), 8.27 (d, J=8.1 Hz, 1H) 9.20 (s, 1H).

LC/MS: measurement condition 2, retention time=1.72 min

LC/MS(ESI+) m/z; 362 [M+H]+

Ex5

$^1$H-NMR (CDCl$_3$) δ: 1.35-1.47 (m, 2H), 1.75-1.91 (m, 3H), 2.10-2.22 (m, 2H), 2.30-2.40 (m, 2H), 3.58 (d, J=5.9 Hz, 2H), 3.87 (q, J=8.6 Hz, 2H) 4.92-5.06 (m, 1H), 6.47 (d, J=7.9 Hz, 1H), 6.77-6.82 (m, 1H), 7.47-7.50 (m, 1H), 7.79 (d, J=8.3 Hz, 1H), 9.44 (s, 1H), 11.90 (bs, 1H),

LC/MS: measurement condition 2, retention time=1.97 min

LC/MS(ESI+) m/z; 380 [M+H]+

Ex6

LC/MS: measurement condition 2, retention time=1.99 min

LC/MS(ESI+) m/z; 394 [M+H]+

Ex7

$^1$H-NMR (DMSO-d$_6$) δ: 1.29-1.49 (m, 2H), 1.67-2.16 (m, 7H), 2.95-3.24 (m, 2H), 3.64 (dd, J=6.5, 2.3 Hz, 2H), 4.47-4.61 (m, 1H), 4.82-4.97 (m, 1H), 6.21 (d, J=7.8 Hz, 1H), 6.80 (d, J=3.3 Hz, 1H), 7.58 (d, J=2.7 Hz, 1H), 8.16 (d, J=8.4 Hz, 1H), 9.01 (s, 1H), 12.31 (br s, 1H).

LC/MS: measurement condition 2, retention time=1.88 min

LC/MS(ESI+) m/z; 419 [M+H]+

LC/MS(ESI−) m/z; 417 [M−H]−

Pharmacological Assay

Now, a pharmacological assay of the tricyclic pyrimidine compounds of the present invention will be described.

1. Enzyme Assay

The JAK inhibitory activities of compounds of the present invention were measured.

The enzymes (JAK1, JAK2, JAK3 and Tyk2) were purchased from Carna Biosciences, Inc.

As the substrate for the enzymes (hereinafter referred to as the substrate), LANCE Ultra ULight-JAK-1 (Tyr1023) Peptide (manufactured by PerkinElmer Co., Ltd.) was used.

As the antibody for detecting phosphorylation of the substrate, LANCE Ultra Europium-anti-phospho tyrosine antibody (PT66) (manufactured by Perkin Elmer Co., Ltd.) was used.

The other reagents are purchased from the following suppliers.

Adenosine triphosphate (ATP): Sigma-Aldrich 4-(2-Hydroxyethyl)-1-piperazineethanesulfonic acid (HEPES): DOJINDO Laboratories Glycol ether diamine tetraacetic acid (EGTA): DOJINDO LABORATORIES Magnesium chloride (MgCl) Wake Pure Chemical Industries, Ltd.

Dithiothreitol (OTT): Wako Pure Chemical Industries, Ltd.

Tween 20: Sigma-Aldrich

Ethylenediaminetetraacetic acid (EDTA): DOJINDO LABORATORIES

The compounds of the present invention, the enzymes (JAK1, JAK2, JAK3 and Tyk2), the substrate and ATP were used for the assays after diluted with the assay buffer.

The composition of the assay buffer is given below.

HEPES (pH7.5): 50 mM
EGTA: 1 mM
MgCl$_2$: 10 mM
DTT: 2 mM
Tween 20: 0.01% (wt/wt)

Dilutions were made at such concentrations and dispensed on a well plate, which will be described later, in such volumes that the following final concentrations would be achieved on the well plate.

Each compound was used at six consecutive concentrations among the 11 concentrations of 1 µM, 0.3 µM, 0.1 µM, 0.03 µM, 0.01 µM, 0.003 µM, 0.001 µM, 0.0003 µM, 0.0001 µM, 0.00003 µM and 0.00001 µM.

The enzyme concentrations and the ATP concentrations in the respective enzyme (JAK1, JAK2, JAK3 and Tyk2) assays were as follows.

JAK1 enzyme assay; the enzyme concentration was 0.5 µg/mL, and the ATP concentration was 70 µM.

JAK2 enzyme assay; the enzyme concentration was 0.013 µg/mL, and the ATP concentration was 10 µM.

JAK3 enzyme assay; the enzyme concentration was 0.020 µg/mL, and the ATP concentration was 3 µM.

Tyk2 enzyme assay; the enzyme concentration was 0.25 µg/mL and the ATP concentration was 20 µM.

The concentration of the substrate for the enzymes was 25 nM.

The concentration of EDTA was 15 mM.

The concentration of PT66 was 2 nM.

Dilute solutions of compounds and enzymes were dispensed into wells of a 384-well black plate (manufactured by Greiner bio-one) and preincubated at room temperature for 5 minutes.

Then, a dilute solution of the substrate and then a dilute solution of ATP were added, and the plate was incubated at room temperature for 30 minutes.

Then, a dilute solution of EDTA and then a dilute solution of PT66 were added, and the plate was incubated at room temperature for 1 hour.

The fluorescences were measured with ARVO-HTS, and from the plot of logarithm of a compound concentration and Inhibitory activity, the IC$_{50}$ value was calculated.

The results of JAK1, JAK2, JAK3 and Tyk2 enzyme assays of the compounds of Synthetic Examples 1 to 7 are shown in Table 1.

As shown below in Table 1, the compounds of the present invention have favorable inhibitory activity against JAKs.

TABLE 1

| Ex No. | IC$_{50}$ (µM) JAK1 | IC$_{50}$ (µM) JAK2 | IC$_{50}$ (µM) JAK3 | IC$_{50}$ (µM) Tyk2 |
|---|---|---|---|---|
| 1 | 0.00099 | 0.0046 | 0.015 | 0.022 |
| 2 | 0.00035 | 0.0015 | 0.0029 | 0.026 |
| 3 | 0.0017 | 0.0051 | 0.010 | 0.018 |
| 4 | 0.00041 | 0.0019 | 0.0071 | 0.039 |
| 5 | 0.00059 | 0.0020 | 0.0027 | 0.010 |
| 6 | 0.00068 | 0.0016 | 0.0025 | 0.019 |
| 7 | 0.00074 | 0.0020 | 0.0051 | 0.011 |

2. Signal Assay in Rat Whole Blood

The inhibitory activities of the compounds of the present invention obtained in Synthetic Examples 1 and 2 against cytokine signaling via JAK were measured by STAT phosphorylation assay using rat whole blood.

Female Lewis rats were purchased from CHARLES RIVER LABORATORIES JAPAN, INC.

Rat IL-6 was purchased from PeproTech.

FITC (fluorescein isothiocyanate)-labeled anti-CD3 antibody (FITC-CD3) was purchased from eBioscience.

BD Phosflow Lysef Fix Buffer, BD Phosflow Perm Buffer III, BD Pharmingen Stain Buffer and BD Phosflow STAT-1 (pY701) PE (R-Phycoerythrin) fluorescently labeled antibody (hereinafter referred to as BD Phosflow STAT-1) were purchased from BD (Becton, Dickinson and Company).

Dilutions were made at such concentrations and dispensed into tubes, which will be described later, in such volumes that the following final concentrations would be achieved in the tubes.

Each compound was used at three consecutive concentrations of 1 µM, 0.1 µM and 0.01 µM, or 10 µM, 1 µM and 0.1 µM.

The concentration of rat IL-6 was 100 ng/mL.

The concentration of FITC-CD3 was 1 µg/mL.

Blood was collected from the inferior vena cave of a female Lewis rat. The blood and a compound were put into each Costar assay block tube and incubated at 37° C. for 15 minutes, then incubated with FITC-CD3 at 37° C. for 15 minutes, incubated with rat IL-6 at 37° C. for 15 minutes and incubated with 10 times as much of BD Phosflow Lyse/Fix Buffer as the blood at 37° C. for 12 minutes. Centrifugal separation was carried out at 5,884 m/s² for 6 minutes with a centrifugal separator to precipitate the cells, and the supernatants were removed.

The cell pellets were washed with 1 mL of phosphate buffered saline (PBS), then incubated with 0.6 mL of BD Phosflow Perm Buffer III on ice for 30 minutes and centrifuged at 5,884 m/s² for 6 minutes by means of a centrifugal separator to precipitate the cells, and the supernatants were removed.

The cell pellets were washed with 0.3 mL of BD Pharmingen Stain Buffer and incubated with 0.1 mL of BD Pharmingen Stain Buffer and 10 µL of BD Phosflow STAT-1 at room temperature for 30 minutes. After addition of 0.1 mL of BD Pharmingen Stain Buffer, the cells were centrifuged at 5,884 m/s² for 6 minutes by means of a centrifugal separator to precipitate the cells, and the supernatants were removed.

The cell pellets were washed with 0.3 mL of BD Pharmingen Stain Buffer, and 0.12 mL of BD Pharmingen Stain Buffer was added. The cytokine signaling inhibition was measured with FACS CantoII (manufactured by BD) by detecting FITC-labeled CD3 positive T cells and detecting the amount of phosphated STAT-1 protein in the cells as the PE fluorescence. From the plot of the logarithm of a compound concentration and inhibitory activity, the $IC_{50}$ value was calculated. The results of rat whole blood signal assays of the compounds of Synthetic Examples 1 and 2 are shown in Table 2.

TABLE 2

| Ex No. | $IC_{50}$ (µM) |
| --- | --- |
| 1 | 0.39 |
| 2 | 0.27 |

Excellent inhibitory activity in the rat whole blood signal assay is favorable for high effectiveness against diseases against which inhibition of JAK is effective, especially rheumatoid arthritis.

The compounds of the present invention showed excellent inhibitory activities against JAK signaling by cytokine stimulation in rat whole blood by means of the JAK inhibitory activity.

Further, the results of the rat whole blood signal assay of compound A (Example[b] 102), Compound B (Example[b] 116) Compound C (Example[b] 122) and Compound D (Example[b] 127) disclosed in WO2013/024895 are shown in Table 3.

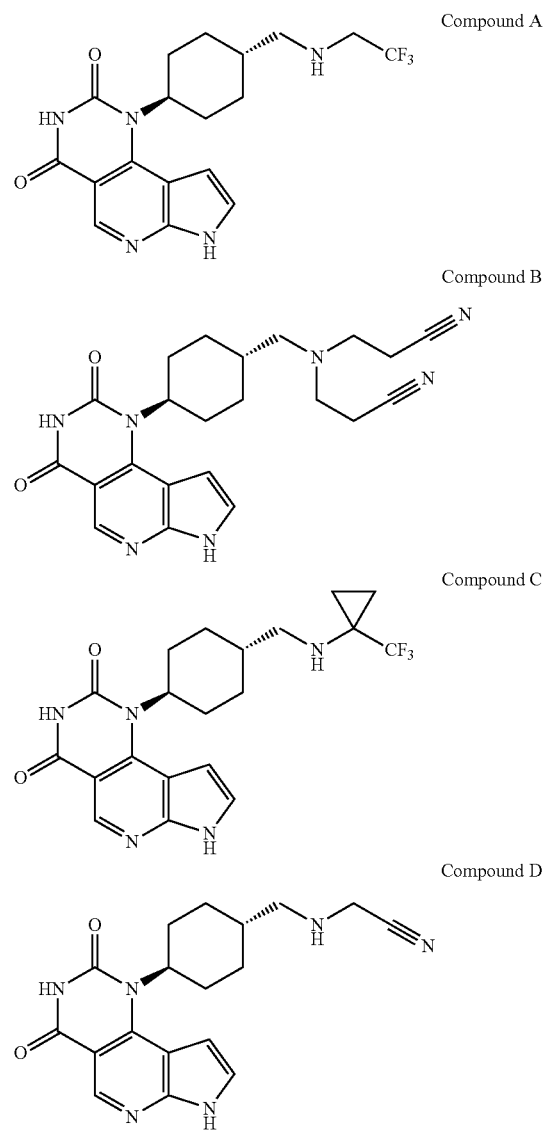

TABLE 3

| Compound | $IC_{50}$ (µM) |
| --- | --- |
| A | 2.4 |
| B | 1.3 |
| C | 1.1 |
| D | 2.7 |

3. Signal Assay in Human Whole Blood

The inhibitory activities of the compounds of the present invention obtained in Synthetic Examples 3 to 7 against cytokine signaling via JAK were measured by STAT phosphorylation assay using human whole blood.

Human whole blood was collected from healthy humans.

Human IL-6 was purchased from R&D systems.

FITC (fluorescein isothiocyanate)-labeled anti-human CD3 antibody (FITC-hCD3) was purchased from BD (Becton, Dickinson and Company).

BD Phosflow Lyse/Fix Buffer, BD Phosflow Perm Buffer III, BD Pharmingen Stain Buffer and BD Phosflow STAT-1 (pY701) PE (R-Phycoerythrin) fluorescently labeled antibody (hereinafter referred to as BD Phosflow STAT-1) were purchased from BD (Becton, Dickinson and Company).

Dilutions were made at such concentrations and dispensed into tubes, which will be described later, in such volumes that the following final concentrations would be achieved in the tubes.

Each compound was used at six concentrations of 3 μM, 1.5 μM, 0.75 μM, 0.38 μM, 0.19 μM and 0.093 μM, at six concentrations of 2 μM, 1 μM, 0.5 μM, 0.25 μM, 0.13 μM and 0.063 μM, or at six concentrations of 10 μM, 5 μM, 2.5 μM, 1.25 μM, 0.63 μM and 0.31 μM.

The concentration of human IL-6 was 100 ng/mL.

Human blood and a compound were put into each Costar assay block tube and incubated at 37° C. for 30 minutes, then incubated with human IL-6 at 37° C. for 15 minutes and incubated with 10 times as much of BD Phosflow Lyse/Fix Buffer as the blood at 37° C. for 12 minutes. Centrifugal separation was carried out at 5,884 m/s² for 6 minutes with a centrifugal separator to precipitate the cells, and the supernatants were removed.

The cell pellets were washed with 1 mL of phosphate buffered saline (PBS), then incubated with 0.6 mL of BD Phosflow Perm Buffer III on ice for 30 minutes and centrifuged at 5,884 m/s² for 6 minutes by means of a centrifugal separator to precipitate the cells, and the supernatants were removed.

The cell pellets were washed with 0.3 mL of BD Pharmingen Stain Buffer and incubated with 0.1 mL of BD Pharmingen Stain Buffer, 10 μL of BD Phosflow STAT-1 and 5 μL of FITC-hCD3 at room temperature for 30 minutes. After addition of 0.1 mL of BD Pharmingen Stain Buffer, the cells were centrifuged at 5,884 m/s² for 6 minutes by means of a centrifugal separator to precipitate the cells, and the supernatants were removed.

The cell pellets were washed with 0.3 mL of BD Pharmingen Stain Buffer, and 0.12 mL of BD Pharmingen Stain Buffer was added. The cytokine signaling inhibition was measured with FACS CantoII (manufactured by BD) by detecting FITC-labeled CD3 positive T cells and detecting the amount of phosphated STAT-1 protein in the cells as the PE fluorescence. From the plot of the logarithm of a compound concentration and inhibitory activity, the $IC_{50}$ value was calculated. The results of human whole blood signal assays of the compounds of Synthetic Examples 3 to 7 are shown in Table 4.

TABLE 4

| Ex No. | $IC_{50}$ (μM) |
|---|---|
| 3 | 0.44 |
| 4 | 0.30 |
| 5 | 0.17 |
| 6 | 0.13 |
| 7 | 0.15 |

Excellent inhibitory activity in the human whole blood signal assay is favorable for high effectiveness against diseases against which inhibition of JAK is effective, especially rheumatoid arthritis.

The compounds of the present invention showed excellent inhibitory activities against JAK signaling by cytokine stimulation in human whole blood by means of the JAK inhibitory activity.

Further, the results of the human whole blood signal assay of Compound E (Example[b] 20), Compound F (Example[b] 69), Compound G (Example[b] 70)), Compound H (Example[b] 106)), Compound I (Example[b] 107) and Compound J (Example[b] 86) disclosed in WO2013/024895 are shown In Table 5.

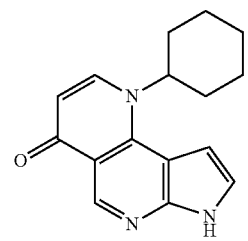

Compound E

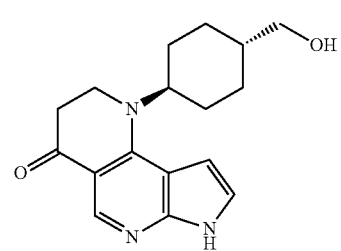

Compound F

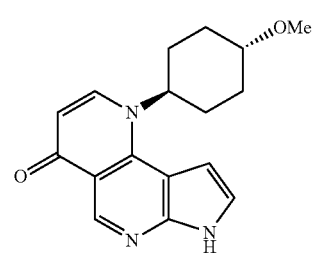

Compound G

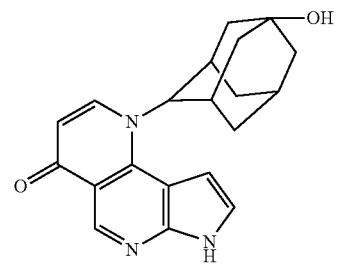

Compound H

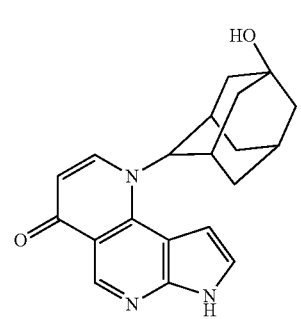

Compound I

Compound J

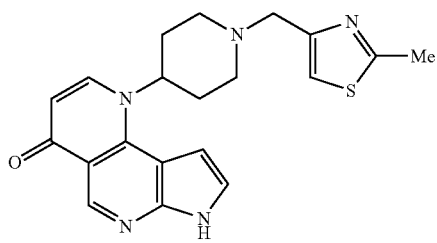

TABLE 5

| Compound | IC$_{50}$ (μM) |
|---|---|
| E | 1.3 |
| F | 5.9 |
| G | 6.5 |
| H | >10 |
| I | >10 |
| J | 7.6 |

4. Inhibition of Proliferation of Erythro-Leukemic Cell Line

The inhibitory activity of the compounds of the present invention on cell proliferation mediated by JAK signal can be assayed using a human erythro-leukemic cell line, TF-1.

TF-1 cells (ATCC (American Type Culture Collection)) can be expanded in RPM11640 media containing 5% fetal bovine serum (hereinafter referred to as FBS) and 1 ng/mL GM-CSF (Granulocyte Macrophage Colony-Stimulating Factor) using a CO$_2$ incubator (5 vol % CO$_2$, 37° C.). At the assay, TF-1 cells washed by PBS (Phosphate Buffered Saline) are resuspended in RPM11640 media containing 5% FBS and seeded on 96-well culture plate at 1×10$^4$ cells/well. Then, a compound is added to each well of the culture plate, and the cells are incubated at 37° C. for 30 minutes. Then, cytokine such as IL-4 or IL-6 is added, and the cells are incubated in a CO$_2$ incubator (5 vol % CO$_2$, 37° C.) for 3 days, Cell proliferation can be assayed using WST-8 reagent (Kishida Chemical Co., Ltd.) according to instructions by the manufacturer. WST-8 reagent is added to each well of the culture plate, and the cells are incubated in a CO$_2$ incubator (5 vol % CO$_2$, 37° C.) for 4 hours. The generated formazan pigment is detected by measuring the absorbance at 450 nm with a microplate reader. From the plot of logarithm of the compound concentrations and the inhibitory activities, the IC$_{50}$ value can be calculated.

5. Oral Absorption Property

A compound having oral absorption property is preferred for treatment of diseases against which JAK inhibition is effective, and the oral absorption property of the compounds of the present invention may be measured using rats as follows.

A compound is suspended in 0.5% methyl cellulose at a concentration of 0.6 mg/mL, and the suspension is forcibly administered orally by a feeding needle to a female Lewis rat (CHARLES RIVER LABORATORIES JAPAN INC.) at a dose of 3 mg/kg/5 mL. Then, blood is sequentially collected through the jugular vein after administration of the compound (after 0.5 to 8 hours) using heparin as an anticoagulant. The collected blood is centrifuged at 17,652 m/s$^2$ for 10 minutes by means of a centrifugal separator to obtain plasma. The plasma is analyzed by liquid chromatography tandem mass spectrometry (LC/MS/MS, manufactured by Waters) to calculate the transition of the concentration of the compound in the plasma after the oral administration (after 0.5 to 8 hours).

6. Effect in Collagen-Induced Rat Arthritis Model

To confirm the therapeutic effect on particularly rheumatoid arthritis among diseases against which JAK inhibition is effective with an experimental animal model, a collagen-induced rat arthritis model may be used (Prostaglandin & other Lipid Mediators, 2001, 66, pp. 317-327) as follows.

Bovine II types collagen solution (Chondrex, Inc.) and incomplete Freund's adjuvant (Difco) are mixed in equal amounts and emulsified to prepare an immune solution. Then, the immune solution is intracutaneously administered to a Lewis female rat (CHARLES RIVER LABORATORIES JAPAN INC.) at 4 portions on the back and one portion on the tail root portion at a dose of 100 μL/portion using a Hamilton syringe. 7 Days after administration of the immune solution, the immune solution is intracutaneously administered similarly again.

The compound to be administered is suspended in 0.5% methyl cellulose at a concentration optionally determined by the IC$_{50}$ value of the cytokine signaling inhibition obtained by the above 2. whole blood signal assay and the concentration of the compound in the blood plasma obtained by the above 5. oral absorption property. The compound suspension thus obtained is orally administered daily after the second administration of the immune solution.

The thickness of the hind-paw swelling in 2 to 3 weeks after the second administration of the immune solution is measured with a caliper to calculate the degree of inhibition of arthritis by the compound.

Now, examples of formulations of compounds of the present invention. In the Formulation Examples 1 to 5, Compound (A) means a compound represented by the formula (I), the formula (II) or the formula (III).

Formulation Example 1

A granule preparation containing the following ingredients is prepared.

| Ingredients | |
|---|---|
| Compound (A) | 10 mg |
| Lactose | 700 mg |
| Corn Starch | 274 mg |
| HPC-L | 16 mg |
| Total | 1000 mg |

A compound (A) and lactose are sifted through a 60-mesh sieve. Corn starch is sifted through a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
|---|---|
| Compound (A) | 10 mg |
| Lactose | 79 mg |
| Corn Starch | 10 mg |
| Magnesium Stearate | 1 mg |
| Total | 100 mg |

A compound (A) and lactose are sifted through a 60-mesh sieve. Corn starch is sifted through a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.

| Ingredients | |
|---|---|
| Compound (A) | 15 mg |
| Lactose | 90 mg |
| Corn Starch | 42 mg |
| HPC—L | 3 mg |
| Total | 150 mg |

A compound (A) and lactose are sifted through a 60-mesh sieve. Corn starch is sifted through a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard gelatin capsules No. 4, 150 mg each

Formulation Example 4

A tablet preparation containing the following ingredients is prepared.

| Ingredients | |
|---|---|
| Compound (A) | 10 mg |
| Lactose | 90 mg |
| Microcrystalline cellulose | 30 mg |
| Magnesium Stearate | 5 mg |
| CMC—Na | 15 mg |
| Total | 150 mg |

A compound (A), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| | |
|---|---|
| Compound (A) | 100 mg |
| Saturated Fatty Add Glyceride | 1000 ml |

Solutions having the above-mentioned composition are usually administered to a patient intravenously at a rate of 1 mL per 1 minute.

INDUSTRIAL APPLICABILITY

The compounds of the present invention have excellent JAK inhibitory activities and are useful for prevention, treatment or improvement of autoimmune diseases, especially rheumatoid arthritis, inflammatory diseases, allergic diseases, cancer and leukemia.

The entire disclosures of Japanese Patent Application No. 2014-100712 filed on May 14, 2014 including specification claims and summary are incorporated herein by reference in its entireties.

The invention claimed is:

1. A compound represented by the formula (III):

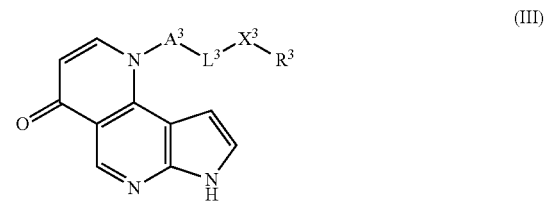

(III)

wherein:
$A^3$ is a $C_{3-7}$ cycloalkylene group,
$L^3$ is a $C_{1-6}$ alkylene group,
$X^3$ is O or NH, and
when $X^3$ is O, $R^3$ is a $C_{1-6}$ haloalkyl group, a cyano $C_{1-6}$ haloalkyl group or a cyano $C_{1-6}$ alkyl group, and
when $X^3$ is NH, $R^3$ is a cyano $C_{1-6}$ haloalkyl group or a cyano $C_{1-6}$ alkyl group,
or a tautomer or pharmaceutically acceptable salt of the compound.

2. The compound, tautomer, or pharmaceutically acceptable salt according to claim 1, wherein $L^3$ is a methylene group.

3. The compound, tautomer, or pharmaceutically acceptable salt according to claim 1, wherein $A^3$ is a cyclohexanediyl group.

4. The compound, tautomer, or pharmaceutically acceptable salt according to claim 1, wherein $X^3$ is O.

5. The compound, tautomer, or pharmaceutically acceptable salt according to claim 4, wherein $R^3$ is a $C_{1-4}$ haloalkyl group or a cyano $C_{1-4}$ haloalkyl group.

6. The compound, tautomer, or pharmaceutically acceptable salt according to claim 1, wherein $X^3$ is NH.

7. The compound, tautomer, or pharmaceutically acceptable salt according to claim 6, wherein $R^3$ is a cyano $C_{1-4}$ haloalkyl group.

8. A composition comprising
the compound, tautomer, or pharmaceutically acceptable salt according to claim 1 as an active ingredient, and
one or more inactive ingredients.

9. The composition according to claim 8, wherein the one or more inactive ingredients comprise at least one selected from the group consisting of lactose, corn starch, low-viscosity hydroxypropylcellulose, magnesium stearate, microcrystalline cellulose, carboxymethylcellulose sodium salt, and saturated fatty acid glyceride.

10. The compound, tautomer, or pharmaceutically acceptable salt according to claim 4, wherein $R^3$ is a 2,2,2-trifluoroethyl group or a 3,3,3-trifluoropropyl group.

11. The compound, tautomer, or pharmaceutically acceptable salt according to claim 4, wherein $R^3$ is a 3-cyano-1,1,1-trifluoropropan-2-yl group or a 2-cyano-1,1,1-trifluoropropan-2-yl group.

12. The compound, tautomer, or pharmaceutically acceptable salt according to claim 1, which is 1-{trans-4-[(2,2,2-Trifluoroethoxy)methyl]cyclohexyl}-1H-pyrrolo[2,3-h][1,6]naphthyridin-4(7H)-one, a tautomer or pharmaceutically acceptable salt thereof.

13. The compound, tautomer, or pharmaceutically acceptable salt according to claim 1, which is 1-{trans-4-[(3,3,3-Trifluoropropoxy)methyl]cyclohexyl}-1H-pyrrolo[2,3-h][1,6]naphthyridin-4(7H)-one, a tautomer or pharmaceutically acceptable salt thereof.

14. The compound, tautomer, or pharmaceutically acceptable salt according to claim 1, which is 4,4,4-Trifluoro-3-{[trans-4-(4-oxo-4,7-dihydro-1H-pyrrolo[2,3-h][1,6]naphthyridin-1-yl)cyclohexyl]methoxy}butanenitrile, a tautomer or pharmaceutically acceptable salt thereof.

15. The compound, tautomer, or pharmaceutically acceptable salt according to claim 1, which is (R)-4,4,4-Trifluoro-3-{[trans-4-(4-oxo-4,7-dihydro-1H-pyrrolo[2,3-h][1,6]naphthyridin-1-yl)cyclohexyl]methoxy}butanenitrile, a tautomer or pharmaceutically acceptable salt thereof.

16. The compound, tautomer, or pharmaceutically acceptable salt according to claim 6, wherein $R^3$ is a 3-cyano-1,1,1-trifluoropropan-2-yl group.

17. The compound, tautomer, or pharmaceutically acceptable salt according to claim 1, which is 4,4,4-Trifluoro-3-({[trans-4-(4-oxo-4,7-dihydro-1H-pyrrolo[2,3-h][1,6]naphthyridin-1-yl)cyclohexyl]methyl}amino)butanenitrile, a tautomer or pharmaceutically acceptable salt thereof.

18. The compound, tautomer, or pharmaceutically acceptable salt according to claim 1, which is (R)-4,4,4-Trifluoro-3-({[trans-4-(4-oxo-4,7-dihydro-1H-pyrrolo[2,3-h][1,6]naphthyridin-1-yl)cyclohexyl]methyl}amino)butanenitrile, a tautomer or pharmaceutically acceptable salt thereof.

* * * * *